United States Patent
Watanabe

(10) Patent No.: US 9,622,718 B2
(45) Date of Patent: Apr. 18, 2017

(54) WIRELESS ULTRASONIC DIAGNOSTIC APPARATUS, WIRELESS ULTRASONIC PROBE, AND PROBE AUTHENTICATION METHOD

(75) Inventor: Yasuhito Watanabe, Osaka (JP)

(73) Assignee: KONICA MINOLTA, INC., Tokyo (JP)

( * ) Notice: Subject to any disclaimer, the term of this patent is extended or adjusted under 35 U.S.C. 154(b) by 524 days.

(21) Appl. No.: 13/001,821

(22) PCT Filed: Apr. 22, 2010

(86) PCT No.: PCT/JP2010/002892
§ 371 (c)(1),
(2), (4) Date: Dec. 29, 2010

(87) PCT Pub. No.: WO2010/122791
PCT Pub. Date: Oct. 28, 2010

(65) Prior Publication Data
US 2011/0105904 A1    May 5, 2011

(30) Foreign Application Priority Data

Apr. 24, 2009  (JP) ................................. 2009-105983

(51) Int. Cl.
*A61B 8/00* (2006.01)
*G01S 7/52* (2006.01)
*G01S 7/00* (2006.01)

(52) U.S. Cl.
CPC .............. *A61B 8/00* (2013.01); *A61B 8/4438* (2013.01); *A61B 8/4472* (2013.01); *A61B 8/56* (2013.01); *G01S 7/5205* (2013.01); *G01S 7/003* (2013.01)

(58) Field of Classification Search
CPC ............ C03B 2201/12; C03B 2203/23; C03B 37/01413; C03B 37/01807; A61B 8/00
See application file for complete search history.

(56) References Cited

U.S. PATENT DOCUMENTS 4,693,120 A * 9/1987 Robinson ......................... 73/618
5,278,757 A * 1/1994 Hoctor et al. ................ 600/459
(Continued)

FOREIGN PATENT DOCUMENTS

| AU | WO 2009067740 A1 * | 6/2009 | ............... A61B 8/08 |
| CN | 1672639 | 9/2005 | |

(Continued)

OTHER PUBLICATIONS

International Search Report issued Jul. 6, 2010 in International (PCT) Application No. PCT/JP2010/002892.
(Continued)

*Primary Examiner* — Joseph M Santos Rodriguez
(74) *Attorney, Agent, or Firm* — Holtz, Holtz & Volek PC

(57) ABSTRACT

A wireless ultrasonic diagnostic apparatus (30) including a wireless ultrasonic probe (300) and a diagnostic device (400). The wireless ultrasonic probe (300) includes: a wireless transmission unit (306) which wirelessly transmits echo data (352); and an ultrasound transmission unit (303) which transmits pairing ultrasound (351) including probe information for identifying the wireless ultrasonic probe (300). The diagnostic device (400) includes: an ultrasound reception unit (401) which receives the pairing ultrasound (351); a probe information detection unit (402) which detects the probe information (452) from the pairing ultrasound (351); and a wireless reception unit (406) which determines, using the probe information (452), whether or not received data is the echo data (352) wirelessly transmitted by the wireless ultrasonic probe (300).

24 Claims, 19 Drawing Sheets

(56) References Cited

U.S. PATENT DOCUMENTS

| | | | |
|---|---|---|---|
| 5,505,205 A * | 4/1996 | Solomon et al. | 600/459 |
| 6,289,238 B1 * | 9/2001 | Besson et al. | 600/509 |
| 6,995,682 B1 * | 2/2006 | Chen | B66D 1/46 |
| | | | 340/12.22 |
| 7,988,633 B2 * | 8/2011 | Hossack et al. | 600/467 |
| 2004/0015079 A1 | 1/2004 | Berger et al. | |
| 2004/0122315 A1 * | 6/2004 | Krill | 600/437 |
| 2004/0171935 A1 | 9/2004 | Van Creveld et al. | |
| 2006/0268795 A1 * | 11/2006 | Tamaki | 370/338 |
| 2007/0083111 A1 * | 4/2007 | Hossack et al. | 600/437 |
| 2007/0088213 A1 * | 4/2007 | Poland | 600/437 |
| 2008/0114249 A1 | 5/2008 | Randall et al. | |
| 2008/0114255 A1 * | 5/2008 | Schwartz et al. | 600/474 |
| 2008/0194961 A1 * | 8/2008 | Randall | 600/459 |
| 2008/0287835 A1 * | 11/2008 | Zhao et al. | 601/2 |
| 2009/0036780 A1 | 2/2009 | Abraham | |
| 2009/0054769 A1 * | 2/2009 | Satoh | 600/437 |
| 2009/0112099 A1 * | 4/2009 | Kurokawa | 600/459 |
| 2010/0298711 A1 * | 11/2010 | Pedersen | A61B 8/00 |
| | | | 600/459 |
| 2014/0051984 A1 | 2/2014 | Berger et al. | |

FOREIGN PATENT DOCUMENTS

| | | | | |
|---|---|---|---|---|
| EP | 2 101 191 A2 * | 9/2009 | | G01S 7/52 |
| GB | WO 2008/152411 * | 12/2008 | | A61B 5/055 |
| JP | 2006-095071 | 4/2006 | | |
| JP | 2007-244579 | 9/2007 | | |
| JP | 2008-000406 | 1/2008 | | |
| JP | 2008-253500 | 10/2008 | | |
| JP | 2008-271383 A | 11/2008 | | |
| JP | 2009-053967 A | 3/2009 | | |
| WO | WO 2008115312 A2 * | 9/2008 | | A61B 8/00 |

OTHER PUBLICATIONS

Japanese Office Action dated Jan. 14, 2014 (and English translation thereof) in counterpart Japanese Application No. 2010-542865.

Extended European Search Report (EESR) dated Mar. 19, 2014 (in English) issued in counterpart European Application No. 10766852.7.

* cited by examiner

FIG. 6

| data | Shape of probe |
|---|---|
| 0x1 | Convex |
| 0x2 | Linear |
| ⋮ | |
| 0xA | Sector |

WIRELESS ULTRASONIC DIAGNOSTIC APPARATUS, WIRELESS ULTRASONIC PROBE, AND PROBE AUTHENTICATION METHOD

TECHNICAL FIELD

The present invention relates to wireless ultrasonic diagnostic apparatuses, wireless ultrasonic probes, and probe authentication methods, and relates particularly to a wireless ultrasonic diagnostic apparatus that includes a wireless ultrasonic probe which wirelessly transmits echo data and a diagnostic device which receives the echo data wirelessly transmitted by the wireless ultrasonic probe.

BACKGROUND ART

Some of conventional wireless ultrasonic diagnostic apparatuses wirelessly transmit echo data obtained by an ultrasonic probe to the main device (see Patent Literature 1, for example).

FIG. 1 shows a structure of a conventional wireless ultrasonic diagnostic apparatus 10 disclosed in Patent Literature 1. A scrambler 112 shown in FIG. 1 scrambles echo data using either unique data identifying a main device 200 or unique data identifying an ultrasonic probe 100. More specifically, the scrambler 112 scrambles serial data provided by a PS conversion unit 110, using either a code signal provided by a code signal generator 114 for identifying the main device 200 or a code signal provided by the code signal generator 114 for identifying the ultrasonic probe 100. Then, the scrambler 112 provides the scrambled data to a modulator 116.

CITATION LIST

Patent Literature

[PTL 1] Japanese Unexamined Patent Application Publication No. 2007-244579

SUMMARY OF INVENTION

Technical Problem

The conventional structure disclosed in Patent Literature 1 enables identification of a specific diagnostic device and a specific wireless ultrasonic probe in one-to-one correspondence using a code signal. However, in some cases, the probe is used with more than one diagnostic device. Thus, if the code signal of the wireless ultrasonic probe corresponds to more than one diagnostic device, plural diagnostic devices respond to one wireless ultrasonic probe. This results in interference.

That is to say, the conventional structure disclosed in Patent Literature 1 does not mention how a plurality of wireless ultrasonic probes are to be concurrently used.

The present invention, conceived to solve the above conventional problem, aims to provide a wireless ultrasonic diagnostic apparatus capable of easily and reliably establishing wireless communication between a diagnostic device and a wireless ultrasonic probe in the case of concurrently using a plurality of wireless ultrasonic probes.

Solution to Problem

In order to solve the conventional problem, the wireless ultrasonic diagnostic apparatus according to an aspect of the present invention is a wireless ultrasonic diagnostic apparatus including: a wireless ultrasonic probe which generates echo data and wirelessly transmits the echo data; and a diagnostic device which receives the echo data wirelessly transmitted by the wireless ultrasonic probe, the wireless ultrasonic probe including: a first signal generator which generates a first signal including probe information for identifying the wireless ultrasonic probe; an ultrasound transmission unit configured to transmit the first signal as first ultrasound; and a wireless transmission unit configured to wirelessly transmit the echo data associated with the probe information, and the diagnostic device including: an ultrasound reception unit configured to receive the first ultrasound transmitted by the wireless ultrasonic probe; a probe information detection unit configured to detect the probe information from the first ultrasound received; and a wireless reception unit configured to receive data that is wirelessly transmitted, and determine, using the probe information detected by the probe information detection unit, whether or not the received data is the echo data wirelessly transmitted by the wireless ultrasonic probe.

With this structure, the wireless ultrasonic diagnostic apparatus according to an aspect of the present invention performs processing (hereinafter referred to as "pairing") to establish wireless communication between the diagnostic device and the wireless ultrasonic probe. Here, the ultrasound does not reach a long distance. Therefore, the wireless ultrasonic probe can transmit the first ultrasound to only the desired diagnostic device even when there is a plurality of diagnostic devices. This enables the wireless ultrasonic diagnostic apparatus according to an aspect of the present invention to easily and reliably establish wireless communication between the diagnostic device and the wireless ultrasonic probe.

In addition, the wireless ultrasonic diagnostic apparatus according to an aspect of the present invention uses, for the purpose of pairing, the ultrasound used for diagnosis, thereby suppressing an increase in cost necessary for adding the above functions.

Furthermore, the wireless ultrasonic probe may further include an operating switch operable by an operator, and when the operating switch is pressed, the first signal generator may generate the first signal, and the ultrasound transmission unit may transmit the first signal as the first ultrasound.

With this structure of the wireless ultrasonic diagnostic apparatus according to an aspect of the present invention, the operator can perform the pairing through a simple operation of pressing the operating switch provided on the wireless ultrasonic probe.

In addition, the first signal generator may generate the first signal including a synchronizing signal, and the probe information detection unit may be configured to detect the probe information from the first ultrasound by detecting the synchronizing signal included in the first ultrasound received.

This structure enables the wireless ultrasonic diagnostic apparatus according to an aspect of the present invention to easily detect the probe information included in the first ultrasound.

Moreover, the ultrasound transmission unit may be further configured to emit second ultrasound for generating the echo data.

Furthermore, the ultrasound transmission unit may include: a first transducer which transmits the first ultrasound according to the first signal; and a second transducer which emits the second ultrasound, the second transducer being different from the first transducer.

With this structure, the frequency of the first transducer can differ from that of the second transducer. Thus, the wireless ultrasonic diagnostic apparatus according to an aspect of the present invention can set an optimal frequency for the first ultrasound.

Furthermore, the first transducer may have a transmission frequency lower than a transmission frequency of the second transducer.

This structure enables the diagnostic device to receive the first ultrasound transmitted from the wireless ultrasonic probe, even when the diagnostic device and the wireless ultrasonic probe are distant from each other.

In addition, the ultrasound transmission unit may include a transducer which transmits the first ultrasound according to the first signal and emits the second ultrasound.

This structure enables the wireless ultrasonic diagnostic apparatus according to an aspect of the present invention to suppress an increase in cost by using the same transducer for both the transmission of the first ultrasound and the transmission and reception of the second ultrasound.

Moreover, the ultrasound transmission unit may include a plurality of transducers which synchronously transmit the first ultrasound according to the first signal.

This structure increases the signal level of the first ultrasound transmitted from the wireless ultrasonic probe, thereby increasing the possibility of successful communication between the wireless ultrasonic probe and the diagnostic device even when the wireless ultrasonic probe and the diagnostic device are distant from each other.

Furthermore, the ultrasound transmission unit may include a delay circuit which delays, according to a shape of a surface of the wireless ultrasonic probe from which the first ultrasound is emitted, the first signal provided to the transducers so that the first ultrasound synchronously transmitted by the transducers becomes plane waves.

This structure enables the wireless ultrasonic probe according to an aspect of the present invention to transmit data without data turbulence even in the case of using a probe having a curved emitting surface, such as a convex wireless ultrasonic probe.

Moreover, the wireless ultrasonic probe may further include a second signal generator which generates a second signal, the transducers may generate the second ultrasound according to the second signal, and the delay circuit may further delay the second signal to adjust a focal position of the second ultrasound, and provide the delayed second signal to the transducers.

This structure enables the wireless ultrasonic diagnostic apparatus according to an aspect of the present invention to enhance the communication quality while suppressing an increase in cost.

In addition, the wireless ultrasonic probe may include a scan unit configured to perform, when the ultrasound transmission unit emits the second ultrasound, sector scanning in directions in which the second ultrasound is emitted, and when the ultrasound transmission unit emits the first ultrasound, the scan unit may fix a direction in which the first ultrasound is emitted.

This structure enables a sector-scanning wireless ultrasonic probe to reliably perform the pairing.

The ultrasound reception unit may have an acoustic impedance in a range of 1.5 to 2.0 inclusive.

This structure enables the wireless ultrasonic diagnostic apparatus according to an aspect of the present invention to receive the first ultrasound with high sensitivity.

Furthermore, the ultrasound reception unit may include an acoustic lens which adjusts a focal position of the first ultrasound.

This structure enables the wireless ultrasonic diagnostic apparatus according to an aspect of the present invention to receive the first ultrasound with high sensitivity.

Moreover, the diagnostic device may include an error processing unit configured to notify an operator of error occurrence when an error occurs with the probe information transmitted by the wireless ultrasonic probe.

This structure allows the operator to easily recognize a failure in connection between the wireless ultrasonic probe and the diagnostic device.

The error processing unit may be configured to notify the operator of the error occurrence by causing an LED to flash or by changing a color of the LED.

This structure allows the operator to recognize a connection error more quickly.

Furthermore, the error processing unit may be configured to notify the operator of the error occurrence by beeping.

This structure allows the operator to recognize a connection error by a sound, enabling a more quick recognition of the connection error.

Note that the present invention can be realized not only as the above wireless ultrasonic diagnostic apparatus, but also as: a probe authentication method which includes, as steps, the characteristic elements included in the wireless ultrasonic diagnostic apparatus; and a program which causes a computer to execute such characteristic steps. It is apparent that such a program can be distributed via a recording medium such as a CD-ROM and a transmission medium such as the Internet.

In addition, the present invention may also be realized as a wireless ultrasonic probe or a diagnostic device included in the wireless ultrasonic diagnostic apparatus.

Furthermore, the present invention can also be realized as a semiconductor integrated circuit (LSI) which achieves some or all of the functions of the wireless ultrasonic diagnostic apparatus.

Advantageous Effects of Invention

The present invention provides a wireless ultrasonic diagnostic apparatus capable of easily and reliably establishing wireless communication between a diagnostic device and a wireless ultrasonic probe in the case of concurrently using a plurality of wireless ultrasonic probes.

BRIEF DESCRIPTION OF DRAWINGS

FIG. 6 shows a data example of pairing ultrasound according to Embodiment 1 of the present invention.

DESCRIPTION OF EMBODIMENTS

Hereinafter, Embodiment 1 of the present invention is described with reference to the drawings.

Embodiment 1

The wireless ultrasonic diagnostic apparatus according to Embodiment 1 of the present invention pairs a wireless ultrasonic probe with a diagnostic device using ultrasound. By doing so, the wireless ultrasonic diagnostic apparatus according to Embodiment 1 of the present invention can easily and reliably establish wireless communication between the wireless ultrasonic probe and the diagnostic device.

First, an overall structure of the wireless ultrasonic diagnostic apparatus according to Embodiment 1 of the present invention is described.

Figure 1:
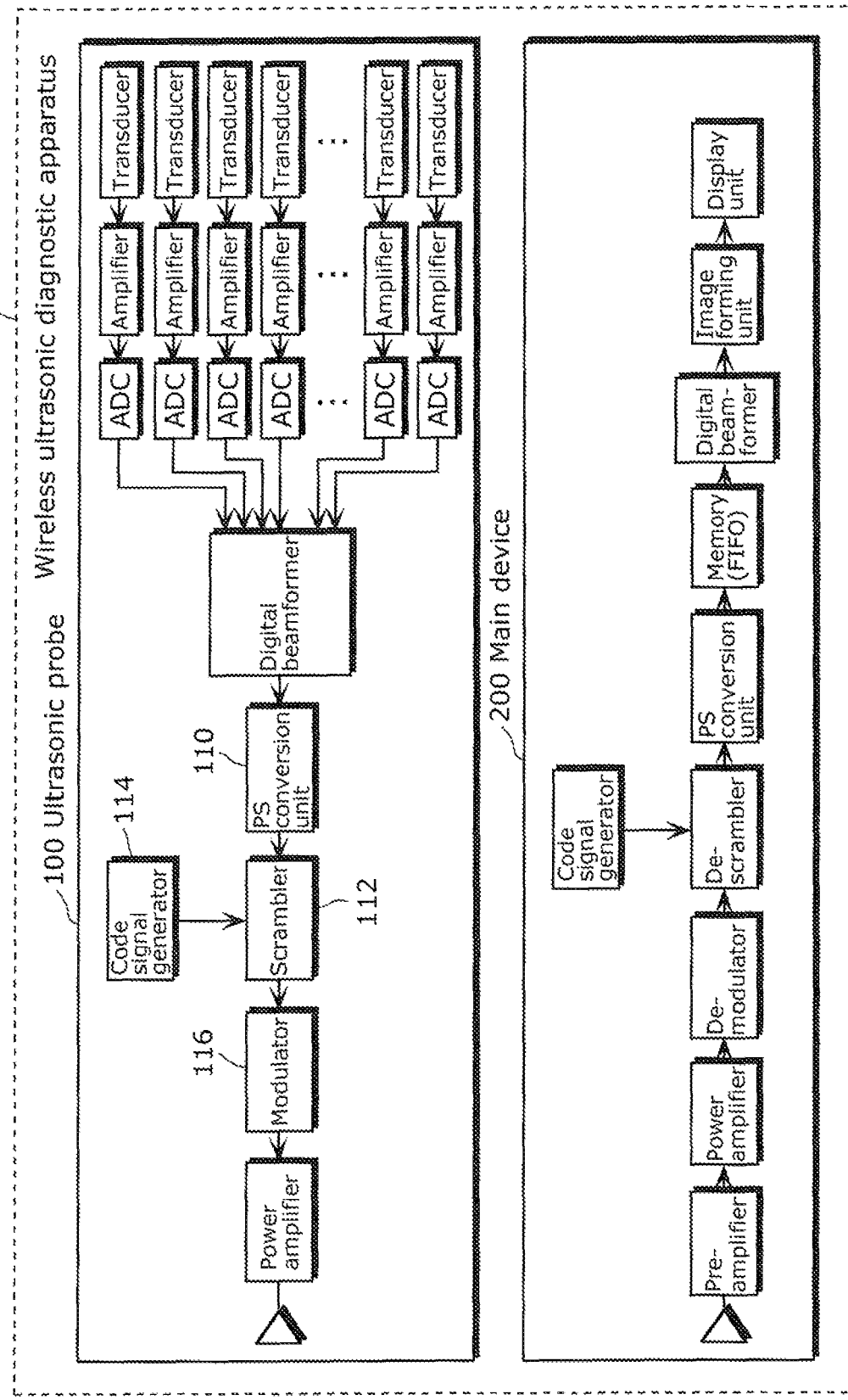
FIG. 1 is a block diagram of a conventional wireless ultrasonic diagnostic apparatus.
Figure 2:
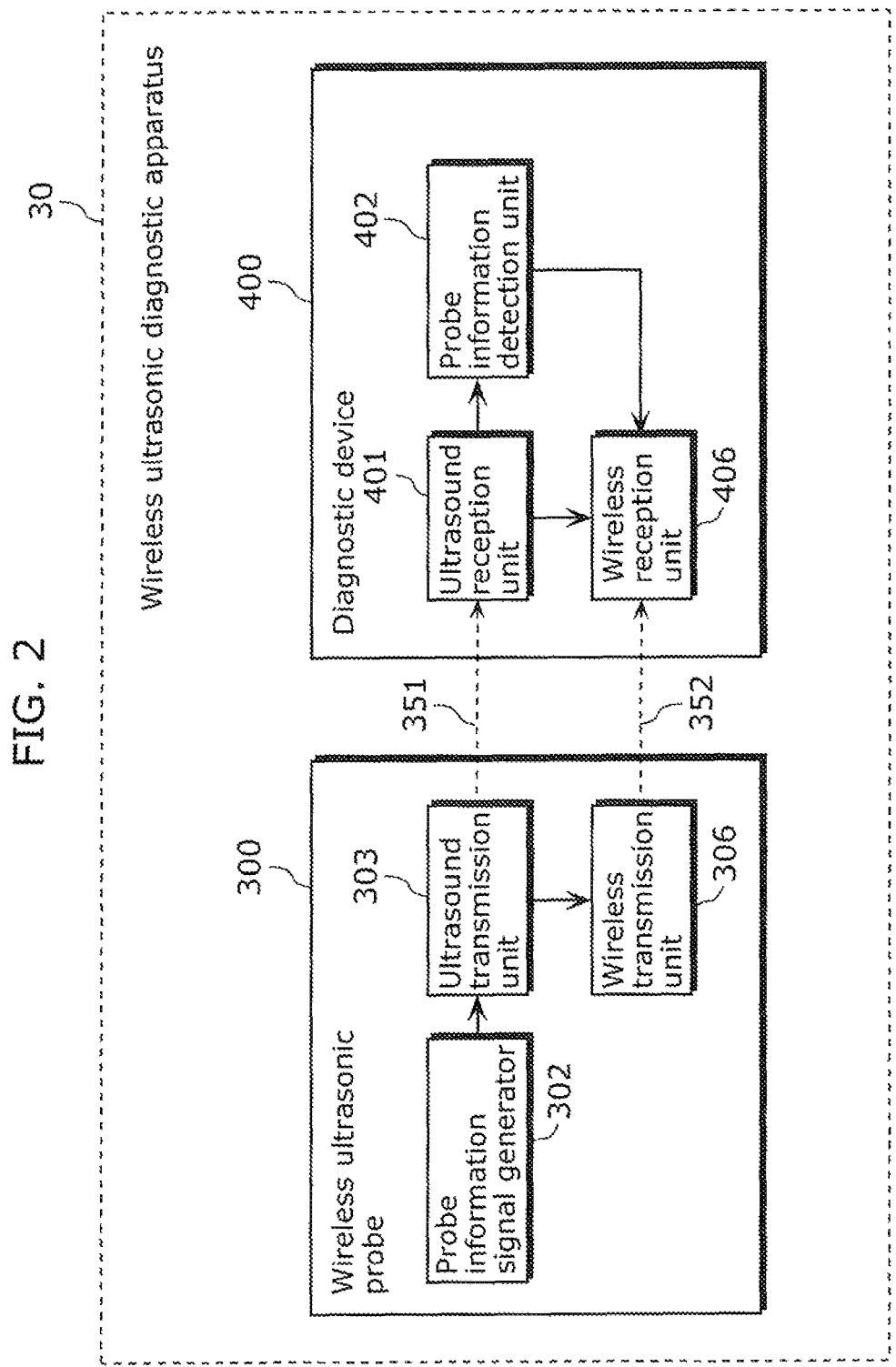
FIG. 2 is a block diagram of a wireless ultrasonic diagnostic apparatus according to Embodiment 1 of the present invention.

FIG. 2 is a block diagram of a wireless ultrasonic diagnostic apparatus 30 according to Embodiment 1 of the present invention. The wireless ultrasonic diagnostic apparatus 30 shown in FIG. 2 includes a wireless ultrasonic probe 300 and a diagnostic device 400.

The wireless ultrasonic probe 300 shown in FIG. 2 wirelessly transmits echo data 352 to the diagnostic device 400. The wireless ultrasonic probe 300 includes: a wireless transmission unit 306 which wirelessly transmits the echo data 352; a probe information signal generator 302 (a first signal generator) which generates a probe information signal including probe information for identifying the wireless ultrasonic probe 300; and an ultrasound transmission unit 303 which transmits the probe information signal as pairing ultrasound 351 (first ultrasound).

The diagnostic device 400 shown in FIG. 2 receives the echo data 352 wirelessly transmitted by the wireless ultrasonic probe 300. The diagnostic device 400 includes: an ultrasound reception unit 401 which receives the pairing ultrasound 351 transmitted by the wireless ultrasonic probe 300; a probe information detection unit 402 which detects the probe information from the pairing ultrasound 351; and a wireless reception unit 406 which identifies, using the probe information detected by the probe information detection unit 402, the echo data 352 wirelessly transmitted from the wireless ultrasonic probe 300.

Hereinafter, a structure of the wireless ultrasonic probe 300 is described in detail.

Figure 3:
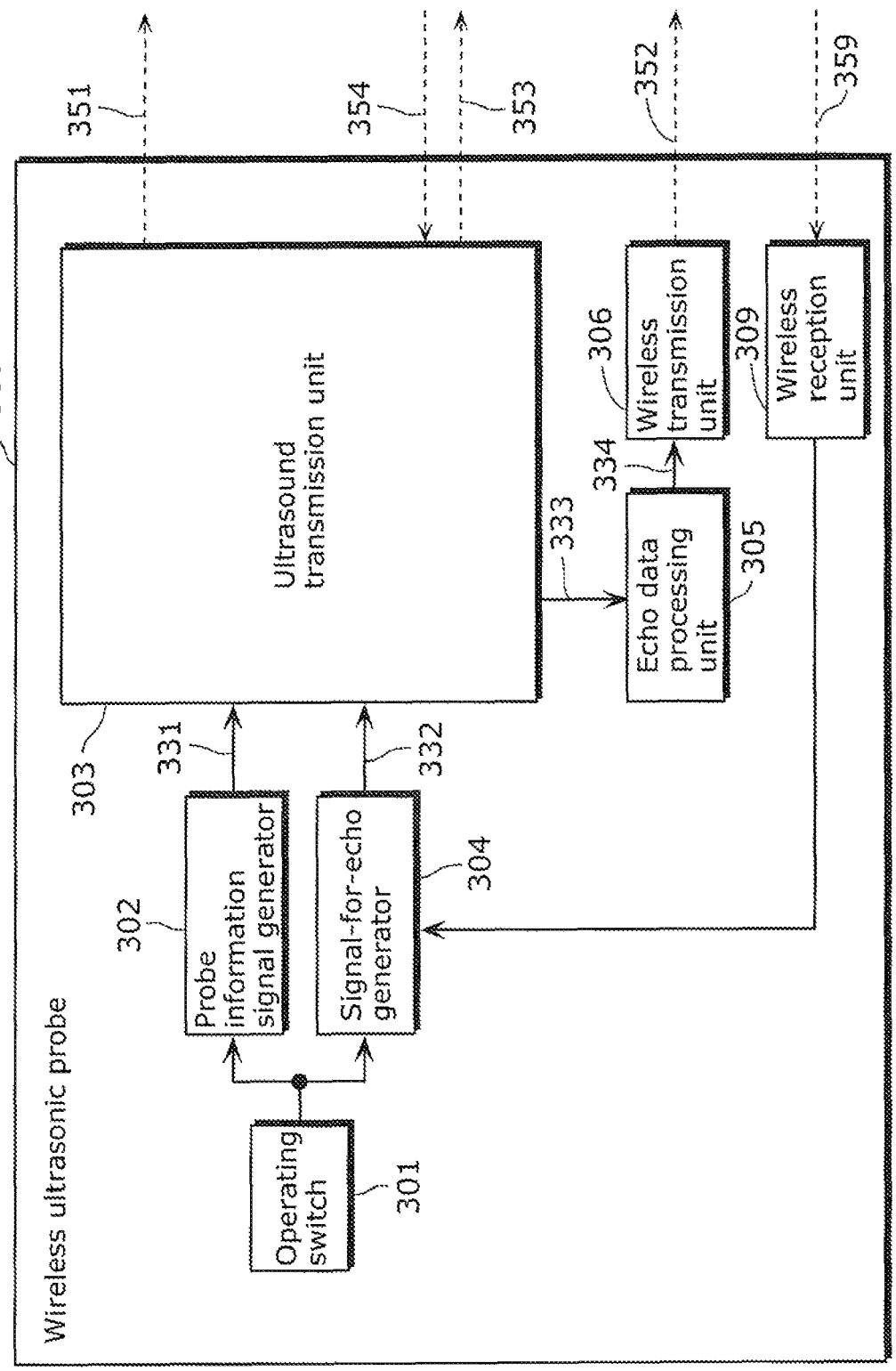
FIG. 3 is a block diagram of a wireless ultrasonic probe according to Embodiment 1 of the present invention.

FIG. 3 is a block diagram showing a detailed structure of the wireless ultrasonic probe 300.

The wireless ultrasonic probe 300 transmits echo ultrasound 353 (second ultrasound) to a subject (a patient, for example), and receives reflected waves 354 (echo) which are the echo ultrasound 353 reflected from the subject. Furthermore, the wireless ultrasonic probe 300 wirelessly transmits, to the diagnostic device 400, the echo data 352 which is based on the reflected waves 354 received.

The wireless ultrasonic probe 300 shown in FIG. 3 includes an operating switch 301 operable by an operator, the probe information signal generator 302, the ultrasound transmission unit 303, a signal-for-echo generator 304 (a second signal generator), an echo data processing unit 305, the wireless transmission unit 306, and a wireless reception unit 309.

Figure 4:
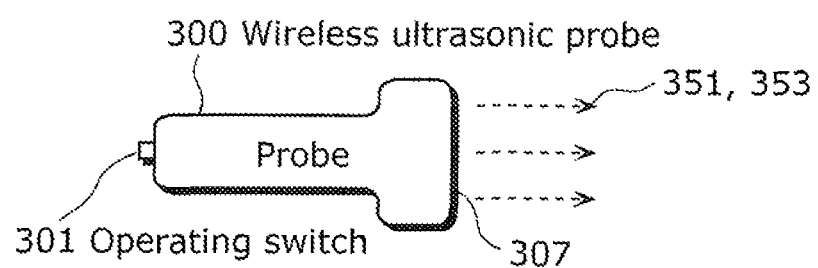
FIG. 4 is an external view of a wireless ultrasonic probe according to Embodiment 1 of the present invention.

FIG. 4 is an external view of the wireless ultrasonic probe 300.

The operating switch 301 is a button, for example. When the operator presses the button, the pairing ultrasound 351 which is low in power is output from the wireless ultrasonic probe 300, and the pairing of the wireless ultrasonic probe 300 with the diagnostic device 400 starts.

The button of the operating switch 301 is desirably provided at a position out of the way of diagnosis. For example, as shown in FIG. 4, the button may be provided on a side opposite to an emitting surface 307 from which the pairing ultrasound 351 and the echo ultrasound 353 are emitted.

When the operating switch 301 is pressed, the probe information signal generator 302 generates a probe information signal 331 including the probe information for identifying the wireless ultrasonic probe 300.

The ultrasound transmission unit 303 transmits the probe information signal 331 as the pairing ultrasound 351.

Figure 5:
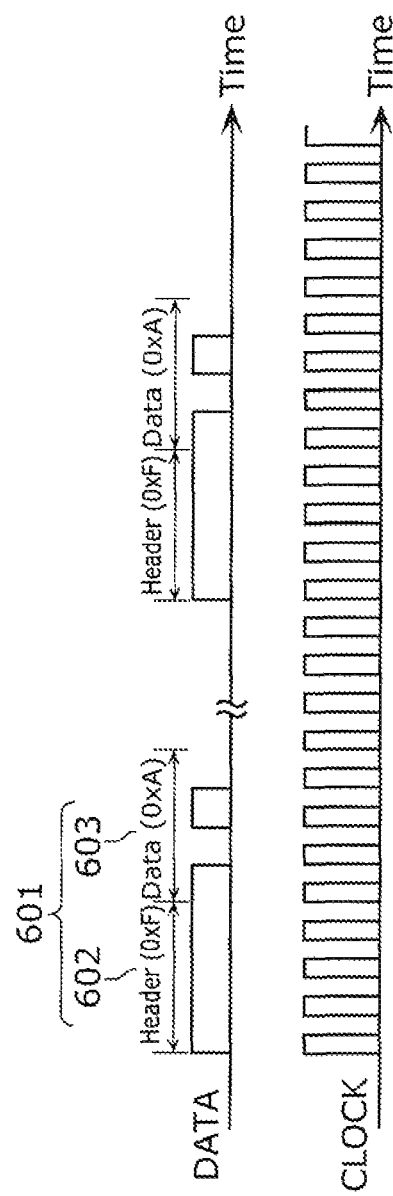
FIG. 5 shows a structural example of pairing ultrasound according to Embodiment 1 of the present invention.

FIG. 5 shows a structural example of the probe information signal 331 (the pairing ultrasound 351).

As shown in FIG. 5, the probe information signal 331 includes a header portion 602 which is a synchronizing signal and a data portion 603 which is the probe information.

The header portion 602 is added so that the starting point of the data portion 603 can be searched. A data sequence not used in the data portion 603 (0xF in FIG. 5) is used in the header portion 602, so that the header can be distinguished.

The data portion 603 indicates, for example, at least one of information on the shape of the wireless ultrasonic probe 300, information on the compatible frequency band of the wireless ultrasonic probe 300, and information on the individual number of the wireless ultrasonic probe 300.

FIG. 6 shows an example of the data portion 603. FIG. 6 shows a case where the data portion 603 indicates the shape of the wireless ultrasonic probe 300.

More specifically, in FIG. 5, the data portion 603 following the header portion 602 indicates 0xA. The shape of the wireless ultrasonic probe corresponding to 0xA is sector, and thus the diagnostic device 400 recognizes that the wireless ultrasonic probe 300 to be connected with is of a sector type. Furthermore, by transmitting the individual number of the wireless ultrasonic probe 300, it is possible to make settings on a probe-by-probe basis even if there is more than one wireless ultrasonic probe of the same type (the sector type, for example).

While the operating switch 301 is pressed, the probe information signal generator 302 continuously outputs data signals 601 each of which includes one header portion 602 and one data portion 603 as shown in FIG. 5.

When the pairing is established, the operator releases the operating switch 301 to stop the output of the pairing ultrasound 351. With such a structure by which the output of the pairing ultrasound 351 is automatically stopped when the operator releases the operating switch 301, it is possible to prevent the operating switch 301 from remaining on.

The pairing ultrasound 351 may be output when the operating switch 301 is pressed once, and stopped when the operating switch 301 is pressed once more. In that case, it is desirable to stop the pairing ultrasound 351 after a certain period of time (after the data signal 601 is output a certain number of times).

The signal-for-echo generator 304 generates a signal for echo 332 while the operating switch 301 is not pressed.

The ultrasound transmission unit 303 transmits the probe information signal 331 as the pairing ultrasound 351, and transmits the signal for echo 332 as the echo ultrasound 353. For example, the frequencies of the pairing ultrasound 351 and the echo ultrasound 353 are in a range of 1 M to 20 MHz inclusive.

The ultrasound transmission unit 303 receives the reflected waves 354 that are the echo ultrasound 353 reflected from the subject, and outputs the reflected waves 354 as an echo signal 333.

The echo data processing unit 305 first performs processing such as signal amplification and A/D conversion on the echo signal 333, and then associates the resultant signal with the probe information so as to generate echo data 334. For example, the echo data processing unit 305 generates the echo data 334 by adding to the echo signal 333 identification information corresponding to the probe information. Note that the echo data processing unit 305 may generate the echo data 334 by scrambling and compressing the echo signal 333 using a predetermined code corresponding to the probe information.

The wireless transmission unit 306 performs such processing as modulation and power amplification on the echo data 334, and wirelessly transmits the resultant data as the echo data 352. The frequency used for the wireless transmission of the echo data 352 is several GHz, for example.

The wireless reception unit 309 receives a control signal 359 wirelessly transmitted by the diagnostic device 400. According to the control signal 359 received by the wireless reception unit 309, the signal-for-echo generator 304 changes the signal for echo 332 to be generated.

Next, a detailed structure of the diagnostic device 400 is described.

Figure 7:
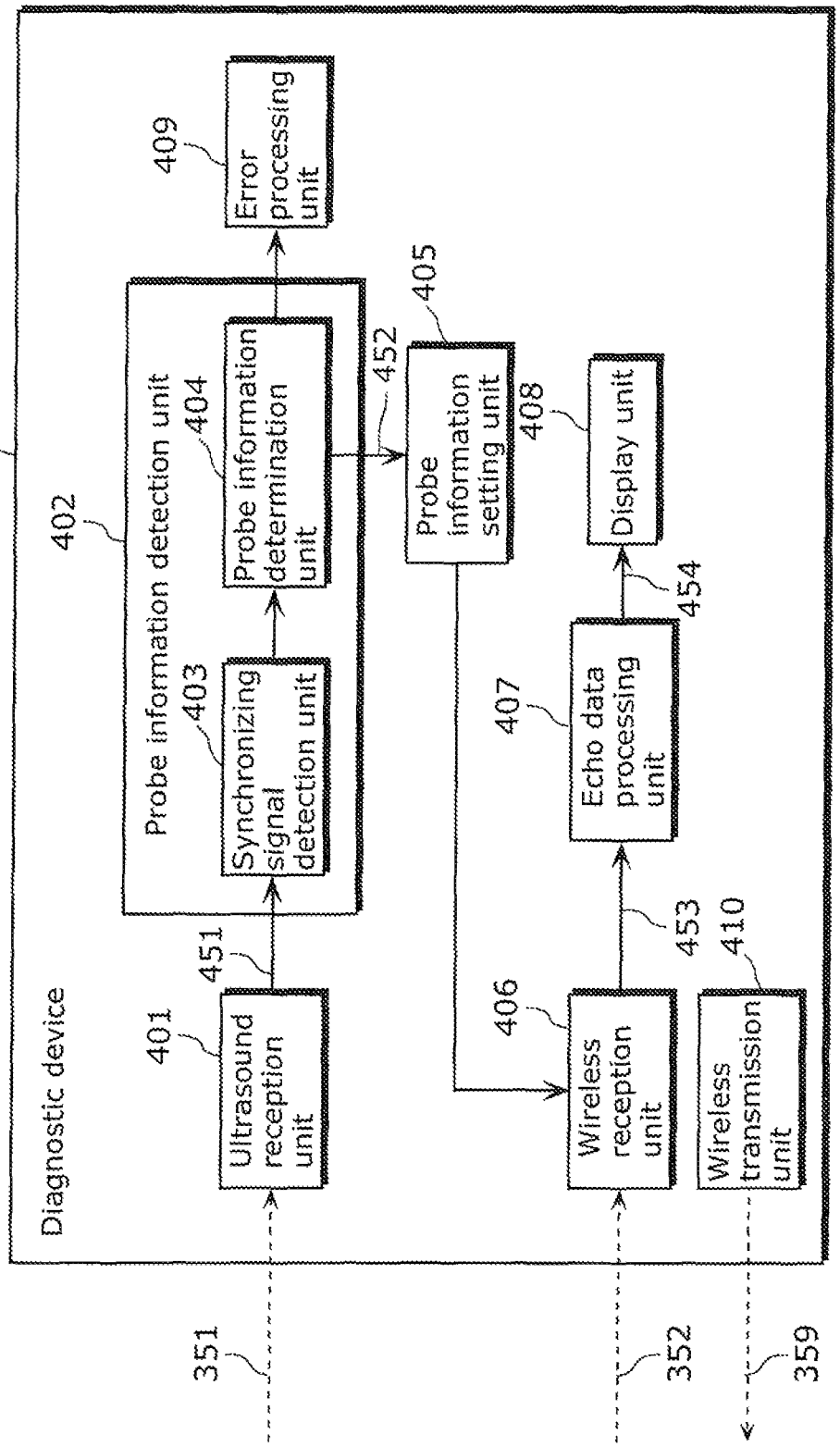
FIG. 7 is a block diagram of a diagnostic device according to Embodiment 1 of the present invention.

FIG. 7 is a block diagram showing the detailed structure of the diagnostic device 400.

The diagnostic device 400 includes the ultrasound reception unit 401, the probe information detection unit 402, a probe information setting unit 405, the wireless reception unit 406, an echo data processing unit 407, a display unit 408, an error processing unit 409, and a wireless transmission unit 410. The probe information detection unit 402 includes a synchronizing signal detection unit 403 and a probe information determination unit 404.

The ultrasound reception unit 401 receives the pairing ultrasound 351 transmitted by the wireless ultrasonic probe 300, and outputs the pairing ultrasound 351 as a probe information signal 451.

Figure 8:
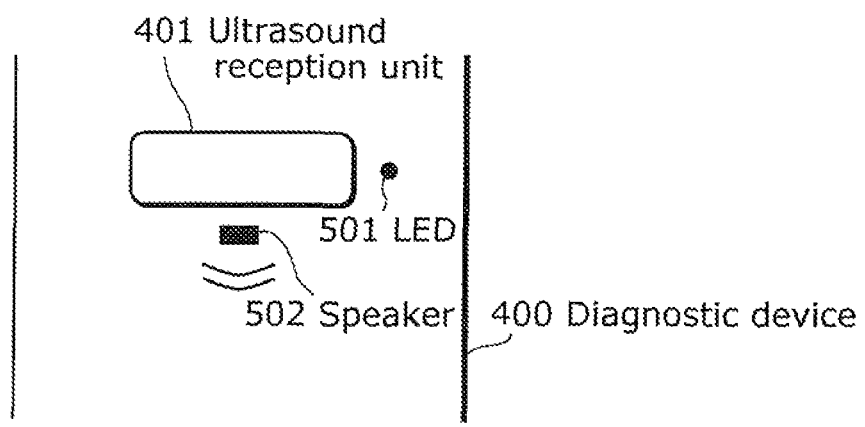
FIG. 8 is an external view of a diagnostic device according to Embodiment 1 of the present invention.

FIG. 8 is an external view of the diagnostic device 400. As shown in FIG. 8, the diagnostic device 400 includes an LED 501 and a speaker 502.

Figure 9:
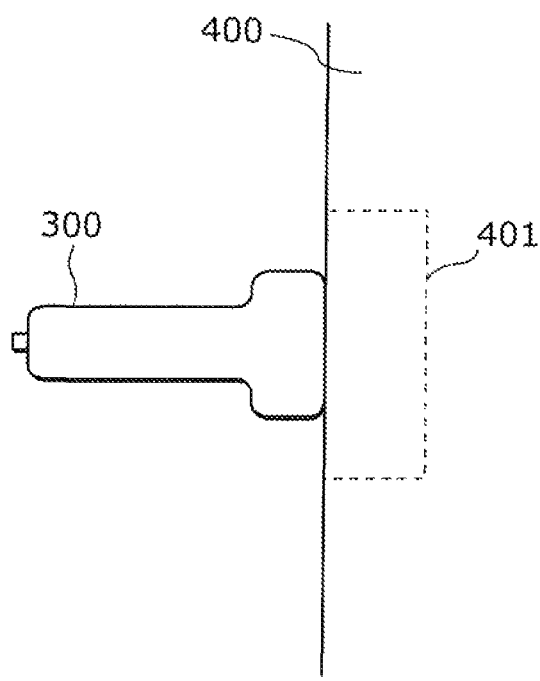
FIG. 9 shows pairing performed in a wireless ultrasonic diagnostic apparatus according to Embodiment 1 of the present invention.

Here, to perform the pairing, the operator presses the operating switch 301 while allowing the wireless ultrasonic probe 300 to contact the ultrasound reception unit 401 provided in the diagnostic device 400 as shown in FIG. 9. With this, the ultrasound reception unit 401 receives the pairing ultrasound 351 transmitted by the wireless ultrasonic probe 300.

The acoustic impedance of the ultrasound reception unit 401 is desirably similar to that of the body, water, or a gel applied to the tested area at the time of echo diagnosis. For example, the acoustic impedance of the ultrasound reception unit 401 is preferably in a range of 1 to 10 inclusive, more preferably in a range of 1.5 to 2.0 inclusive.

This reduces the difference between the acoustic impedance of the wireless ultrasonic probe 300 and that of the ultrasound reception unit 401, allowing the ultrasound reception unit 401 to reliably receive the pairing ultrasound 351 transmitted from the wireless ultrasonic probe 300.

The synchronizing signal detection unit 403 detects the synchronizing signal (the header portion 602) included in the probe information signal 451.

The probe information determination unit 404 obtains, based on the synchronizing signal detected by the synchronizing signal detection unit 403, probe information 452 (the data portion 603) included in the probe information signal 451. Furthermore, the probe information determination unit 404 determines whether or not an error has occurred with the probe information signal 451.

Based on the probe information 452 obtained by the probe information determination unit 404, the probe information setting unit 405 makes settings of the pairing of the wireless ultrasonic probe 300 with the diagnostic device 400, so as to enable identification of the echo data 352 transmitted from the wireless ultrasonic probe 300.

Based on the probe information 452 obtained by the probe information determination unit 404, the probe information setting unit 405 also makes settings of the operations of the wireless ultrasonic probe 300 and the diagnostic device 400. With this, connection is established between the wireless ultrasonic probe 300 and the diagnostic device 400, and the settings of the wireless ultrasonic probe 300 and the diagnostic device 400 are completed.

Note that when the connection is established, the diagnostic device 400 may notify the operator of the establishment of the connection by changing the color of the LED 501 (from red to blue, for instance). When the connection is established, the diagnostic device 400 may also notify the operator of the establishment of the connection by lighting up the LED 501, for example. Furthermore, the diagnostic device 400 may also notify the operator of the establishment of the connection by emitting, from the speaker 502, a sound indicating the connection establishment.

When an error has occurred with the probe information signal 451, the error processing unit 409 notifies the operator of the error occurrence. More specifically, the error processing unit 409 performs the error notification in such cases as where the synchronizing signal (the header portion 602) is not detected even though the ultrasound signal is detected or where the value of the data portion 603 is outside a specified value range even though the ultrasound signal is detected. In addition, the error processing unit 409 performs the error notification using either the LED 501 or the speaker 502. For example, the error processing unit 409 either causes the LED 501 to flash or changes the color of the LED 501. Specifically, the error processing unit 409 may cause the LED 501 to flash in red. Alternatively, the error processing unit 409 may beep through the speaker 502.

In such a manner, the wireless ultrasonic diagnostic apparatus 30 notifies the operator of the connection establishment and the error occurrence using either the LED 501 or the speaker 502. This allows the operator to recognize that the pairing has been reliably completed.

Note that the diagnostic device 400 may include both the LED 501 and the speaker 502, or only one of them.

The wireless reception unit 406 receives the echo data 352 wirelessly transmitted by the wireless ultrasonic probe 300. Furthermore, the wireless reception unit 406 determines, according to the probe information 452 set by the probe information setting unit 405, whether or not the received data is the echo data 352 transmitted by the wireless ultrasonic probe 300 corresponding to the probe information 452 set by the probe information setting unit 405. When the received data is the echo data 352 transmitted by the wireless ultrasonic probe 300 corresponding to the probe information 452 set by the probe information setting unit 405, the wireless reception unit 406 outputs the echo data 352 as echo data 453.

For example, when the wireless ultrasonic probe 300 transmits the echo data 352 including identification information corresponding to the probe information of the wireless ultrasonic probe 300, the wireless reception unit 406 generates the echo data 453 by performing power amplification and demodulation on the echo data 352. Furthermore, the wireless reception unit 406 extracts identification information included in the echo data 453. In addition, when the probe information corresponding to the extracted identification information matches the set probe information 452, the wireless reception unit 406 determines that the echo data 453 is the data transmitted by the paired wireless ultrasonic probe 300, and outputs the echo data 453 to the subsequently-provided echo data processing unit 407.

Furthermore, when the wireless ultrasonic probe 300 transmits the echo data 334 generated through the scrambling and the compression using a predetermined code corresponding to the probe information of the wireless ultrasonic probe 300, the wireless reception unit 406 generates the echo data 453 by performing power amplification and demodulation on the echo data 352 and then performing descrambling and decompression using a predetermined code corresponding to the probe information 452. In this case, the wireless reception unit 406 can correctly reconstruct only the echo to data 352 transmitted by the paired wireless ultrasonic probe 300.

The echo data processing unit 407 generates image data 454 from the echo data 453.

The display unit 408 displays the image data 454.

The wireless transmission unit 410 wirelessly transmits the control signal 359 for changing the echo ultrasound 353 emitted by the wireless ultrasonic probe 300.

Next, a flow of the operation of the wireless ultrasonic probe 300 is described.

Figure 10:
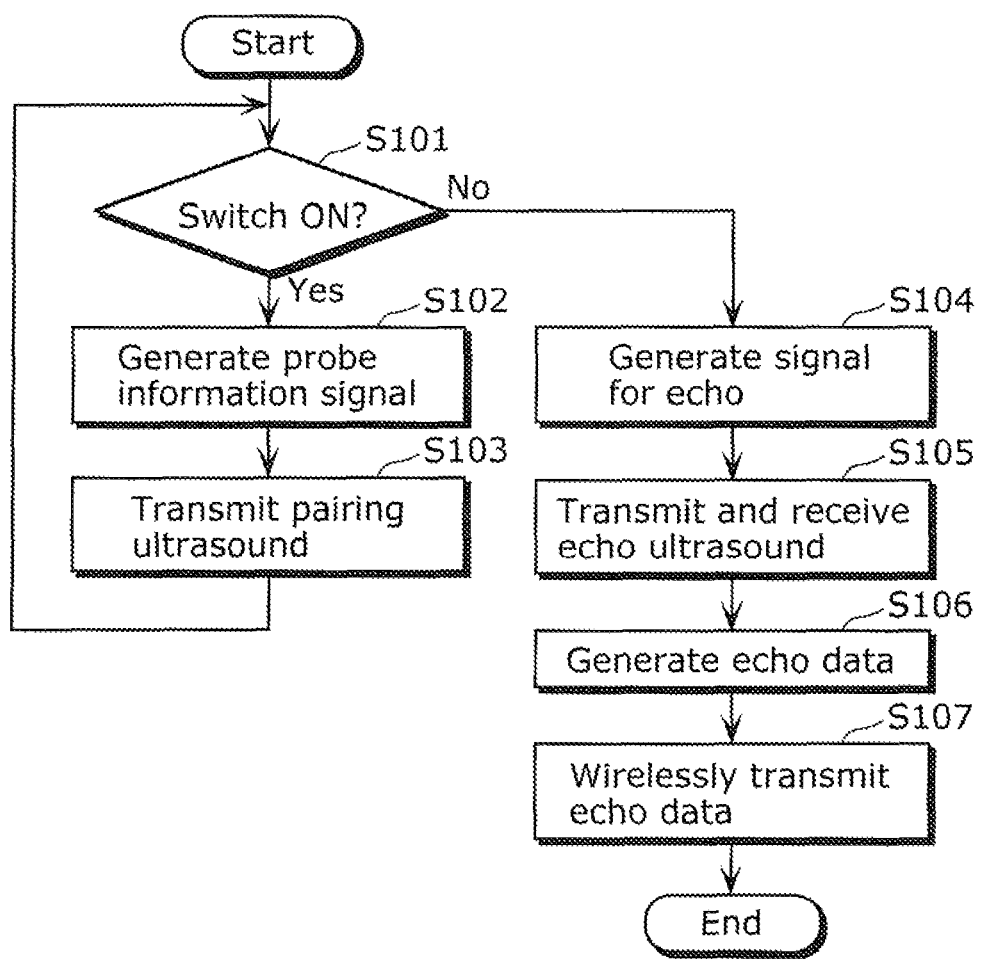
FIG. 10 is a flowchart showing a processing flow of a wireless ultrasonic probe according to Embodiment 1 of the present invention.

FIG. 10 is a flowchart showing the flow of the operation of the wireless ultrasonic probe 300.

As shown in FIG. 10, when the operating switch 301 is on (Yes in S101), the probe information signal generator 302 generates the probe information signal 331 (S102).

Next, the ultrasound transmission unit 303 transmits, as the pairing ultrasound 351, the probe information signal 331 generated by the probe information signal generator 302 (S103).

On the other hand, when the operating switch 301 is off (No in S101), the signal-for-echo generator 304 generates the signal for echo 332 (S104).

Subsequently, the ultrasound transmission unit 303 transmits the signal for echo 332 as the echo ultrasound 353 (S105).

Then, the ultrasound transmission unit 303 receives the reflected waves 354 that are the echo ultrasound 353 reflected from the subject, and outputs the reflected waves 354 as the echo signal 333. Next, the echo data processing unit 305 generates the echo data 334 from the echo signal 333 (S106).

Subsequently, the wireless transmission unit 306 wirelessly transmits the echo data 334 as the echo data 352 (S107).

Next, a flow of the operation of the diagnostic device 400 is described.

Figure 11:
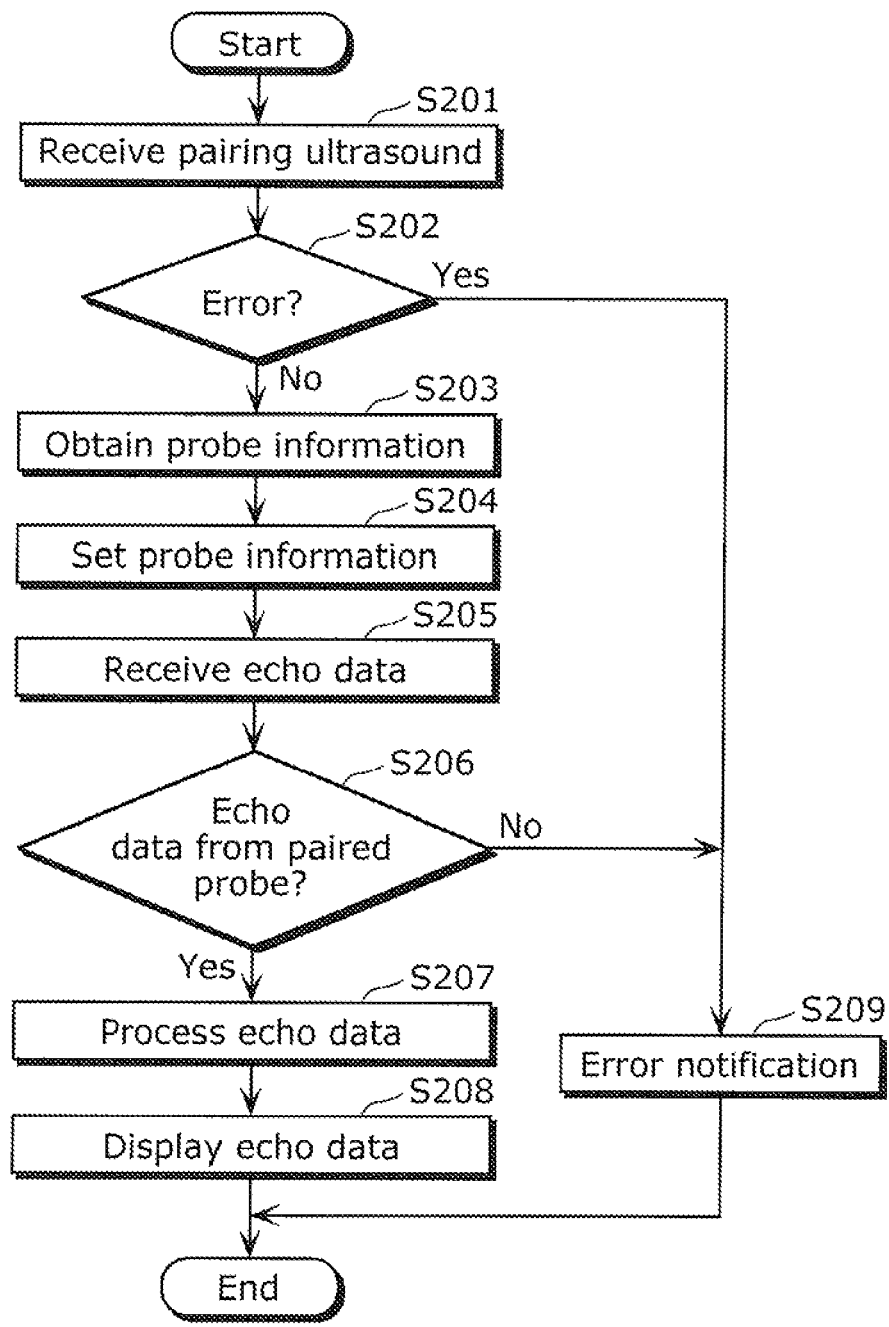
FIG. 11 is a flowchart showing a processing flow of a diagnostic device according to Embodiment 1 of the present invention.

FIG. 11 is a flowchart showing the flow of the operation of the diagnostic device 400.

As shown in FIG. 11, first, the ultrasound reception unit 401 receives the pairing ultrasound 351 and outputs the pairing ultrasound 351 as the probe information signal 451 (S201).

Then, the probe information detection unit 402 determines whether or not an error has occurred with the probe information signal 451 (S202).

When an error has occurred with the probe information signal 451 (Yes in S202), the error processing unit 409 notifies the operator of the error occurrence (S209).

On the other hand, when no error has occurred with the probe information signal 451 (No in S202), the probe information detection unit 402 obtains the probe information 452 included in the probe information signal 451 (S203).

Subsequently, according to the probe information 452, the probe information setting unit 405 makes settings of the pairing of the wireless ultrasonic probe 300 with the diagnostic device 400 (S204).

Next, the wireless reception unit 406 receives the echo data 352 wirelessly transmitted from the wireless ultrasonic probe 300, and generates the echo data 453 from the received echo data 352 (S205).

Then, the wireless reception unit 406 determines whether or not the received echo data 352 is the echo data 352 transmitted from the paired wireless ultrasonic probe 300 (S206).

When the received echo data 352 is not the echo data 352 transmitted from the paired wireless ultrasonic probe 300 (No in S206), the diagnostic device 400 notifies the operator that an error has occurred (S209), and terminates the processing.

On the other hand, when the received echo data 352 is the echo data 352 transmitted from the paired wireless ultrasonic probe 300 (Yes in S206), the echo data processing unit 407 generates the image data 454 from the echo data 453 (S207). Subsequently, the display unit 408 displays the image data 454 (S208).

With the above operations, the wireless ultrasonic diagnostic apparatus 30 according to Embodiment 1 of the present invention pairs the wireless ultrasonic probe 300 with the diagnostic device 400 using ultrasound.

Here, in the case where the pairing is performed through the wireless transmission used for transmitting the echo data 352, another diagnostic device might receive the pairing signal transmitted from the wireless ultrasonic probe, resulting in recognition by the other diagnostic device in error.

In contrast, the pairing ultrasound 351 output from the wireless ultrasonic probe 300 according to Embodiment 1 of the present invention is low in signal level and thus does not reach the diagnostic device located at distance. This prevents recognition by the other diagnostic device in error.

In such a manner, the wireless ultrasonic diagnostic apparatus 30 according to Embodiment 1 of the present invention can reliably pair the wireless ultrasonic probe 300 with the diagnostic device 400.

Another possible approach is to register, in the diagnostic device, information on a plurality of wireless ultrasonic probes in advance, so that the wireless ultrasonic probes can be switched from one to the other through operation on the diagnostic device. When using such a method, it is necessary to make initial settings by, for example, naming each wireless ultrasonic probe, in order to identify a wireless ultrasonic probe for actual use and a wireless ultrasonic probe which is to be selected through the diagnostic device. It is also necessary to put the individual names or the like on the wireless ultrasonic probes, for example, to allow distinction therebetween.

In contrast, the wireless ultrasonic diagnostic apparatus 30 according to Embodiment 1 of the present invention can enable the diagnostic device 400 to recognize only a pairing-target wireless ultrasonic probe 300 through a simple operation of pressing the operating switch 301 while allowing the pairing-target wireless ultrasonic probe 300 to contact the diagnostic device 400. In such a manner, the wireless ultrasonic diagnostic apparatus 30 according to Embodiment 1 of the present invention can easily pair the wireless ultrasonic probe 300 with the diagnostic device 400. Furthermore, the wireless ultrasonic diagnostic apparatus 30 according to Embodiment 1 of the present invention is advantageous in that there is no need to perform, in the diagnostic device, the registration and the initial settings that enable the probe identification.

In addition, the wireless ultrasonic diagnostic apparatus 30 according to Embodiment 1 of the present invention uses, for the purpose of pairing, the ultrasound used for generating the echo data. This enables the wireless ultrasonic diagnostic apparatus 30 to perform the above-described functions while suppressing an increase in cost.

Hereinafter, structural examples of the ultrasound transmission unit 303 are described.

Figure 12:
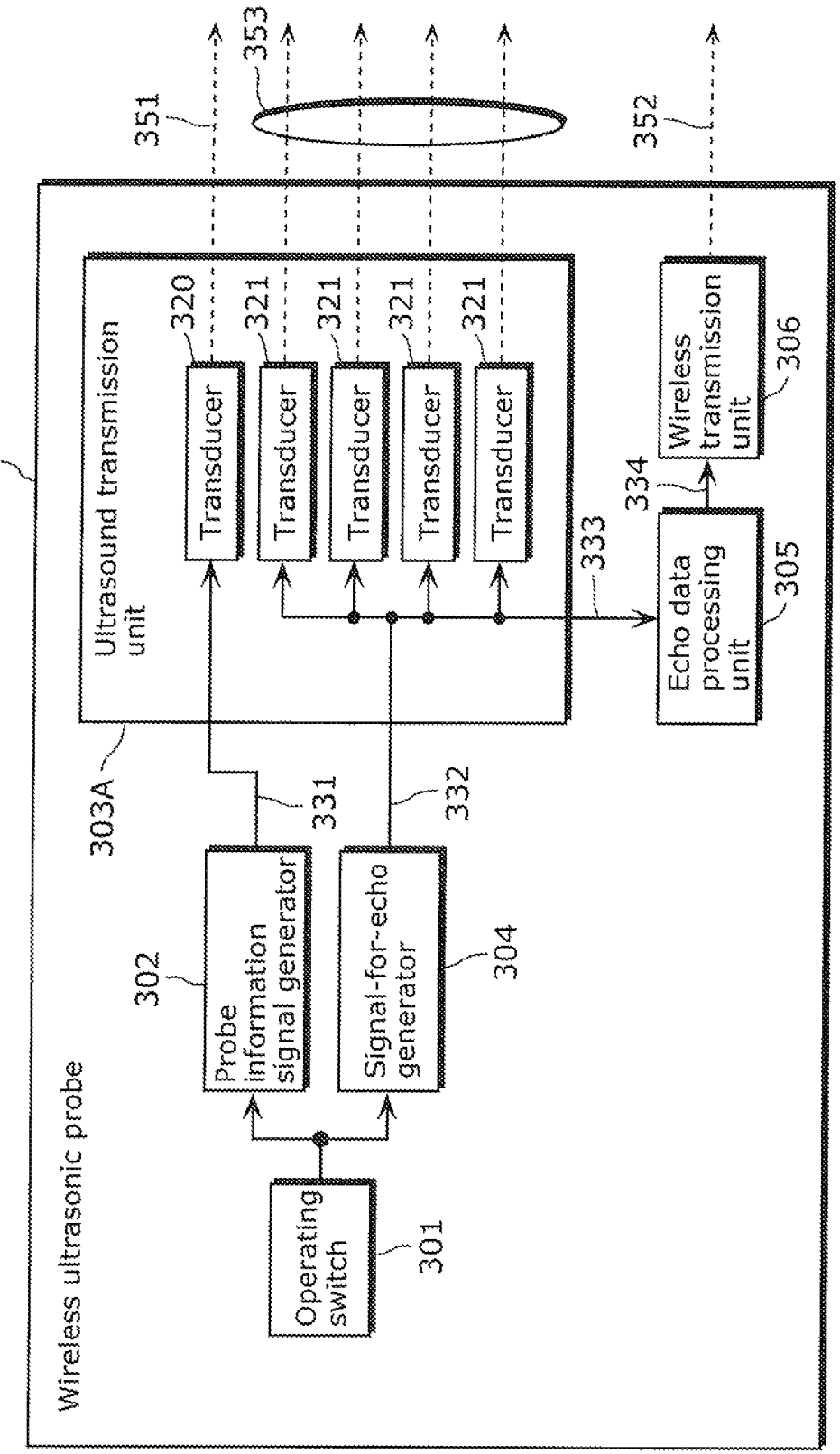
FIG. 12 shows a structure of an ultrasound transmission unit according to Embodiment 1 of the present invention.

FIG. 12 shows a structural example of an ultrasound transmission unit 303A that is an example of the ultrasound transmission unit 303.

The ultrasound transmission unit 303A shown in FIG. 12 includes a transducer 320 and a plurality of transducers 321.

The transducer 320 is used only for the transmission of the pairing ultrasound 351. The transducers 321 are used only for the transmission and reception (emission) of the echo ultrasound 353.

Using the transducer 320 dedicated for the generation of the pairing ultrasound 351 incurs an additional cost for the transducer 320; however, it increases the flexibility of the pairing ultrasound 351. For example, the frequency of the pairing ultrasound 351 can be set lower than that of the echo ultrasound 353. That is to say, the transmission frequency of the transducer 320 may be lower than that of the transducers 321. Here, a lower frequency reduces the amount of attenuation that occurs during propagation through the air. This leads to an increase in the possibility of successful communication between the wireless ultrasonic probe 300 and the diagnostic device 400 using the pairing ultrasound 351 even when they are slightly distant from each other. This means that in the case of using the dedicated transducer 320, the communication between the wireless ultrasonic probe 300 and the diagnostic device 400 is possible by simply bringing them close each other, that is, without making the wireless ultrasonic probe 300 contact the ultrasound reception unit 401.

Note that ultrasound signals are high in frequency and thus have the property of traveling straight without spreading in the lateral direction. For this reason, a wireless ultrasonic probe 300 not in use is placed distantly from the diagnostic device 400, and is usually not positioned along a straight line extending from the reception point of the diagnostic device 400. Therefore, erroneous pressing of the operating switch 301 does not result in recognition of the unused wireless ultrasonic probe 300 by the diagnostic device 400.

Figure 13:
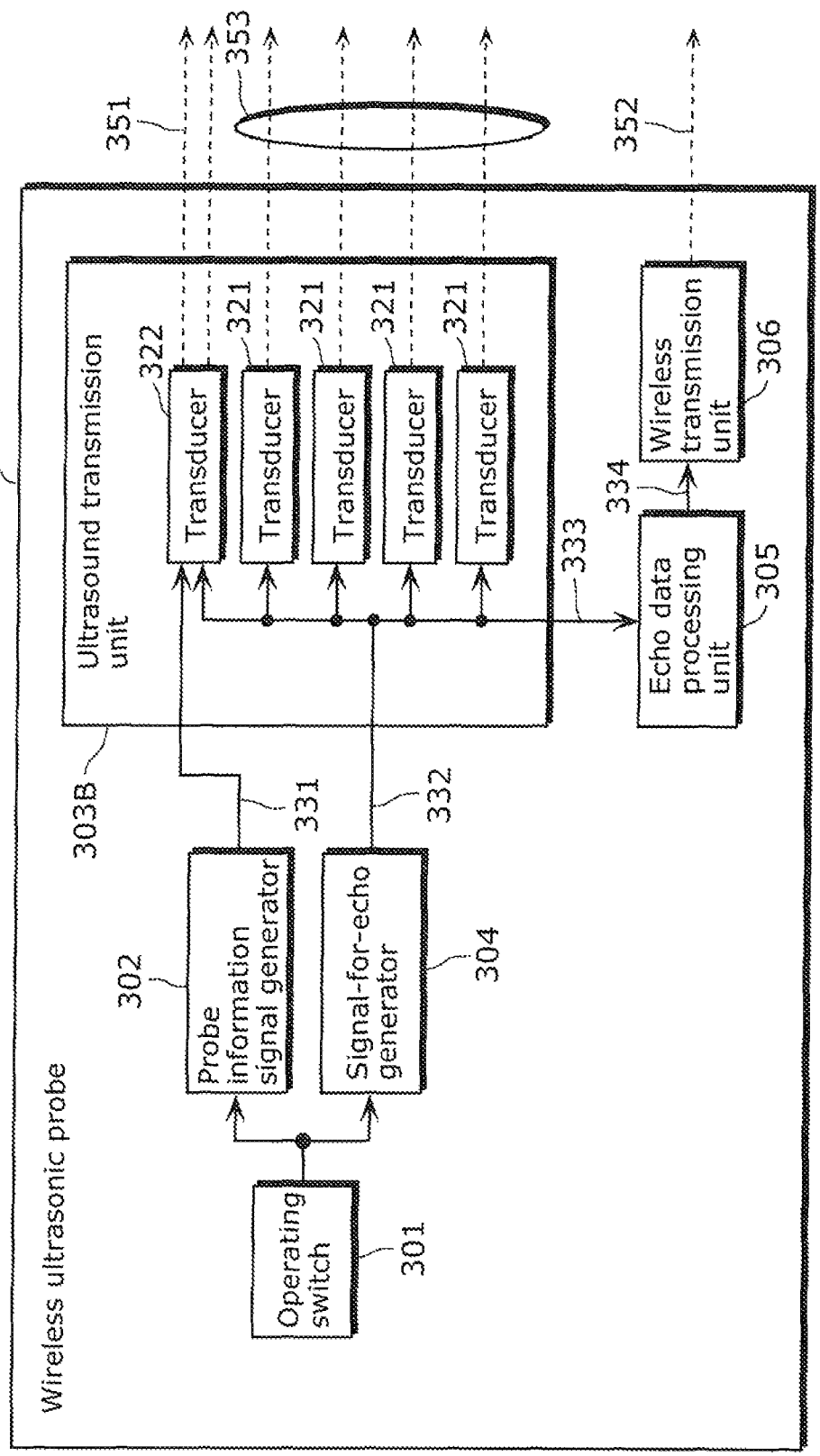
FIG. 13 shows a structure of an ultrasound transmission unit according to Embodiment 1 of the present invention.

FIG. 13 shows a structural example of an ultrasound transmission unit 303B that is another example of the ultrasound transmission unit 303.

The ultrasound transmission unit 303B shown in FIG. 13 includes a transducer 322 and a plurality of transducers 321.

The transducers 321 are used only for the transmission and reception of the echo ultrasound 353. The transducer 322 is used for both the transmission of the pairing ultrasound 351 and the transmission and reception of the echo ultrasound 353.

In the case of using the transducer 322 for the generation of both the pairing ultrasound 351 and the echo ultrasound 353 as described above, no additional cost is necessary for the transducer because the shape thereof remains the same as the conventional one. However, the flexibility in the sound pressure and the frequency of the pairing ultrasound 351 decreases because they are determined based on the echo ultrasound 353.

Note that although the number of the transducers 320 dedicated for the pairing ultrasound 351 is one in FIG. 12, there may be more than one transducer 320.

In addition, although the number of the transducers 322 used for both the pairing ultrasound 351 and the echo ultrasound 353 is one in FIG. 13, there may be more than one transducer 322. Furthermore, all the transducers included in the ultrasound transmission unit 303B may be used for both the pairing ultrasound 351 and the echo ultrasound 353.

The number of transducers 321 that are shown in FIGS. 12 and 13 and used for generating the echo ultrasound 353 is a mere example, and there may be more or less transducers 321. The number of transducers 321 may be one.

Furthermore, the diagnostic device 400 may reset the pairing when the wireless ultrasonic probe 300 is switched off and the echo data 352 is no longer transmitted to the diagnostic device 400.

Embodiment 2

Embodiment 2 of the present invention describes a variation of the wireless ultrasonic probe 300 according to Embodiment 1.

Figure 14:
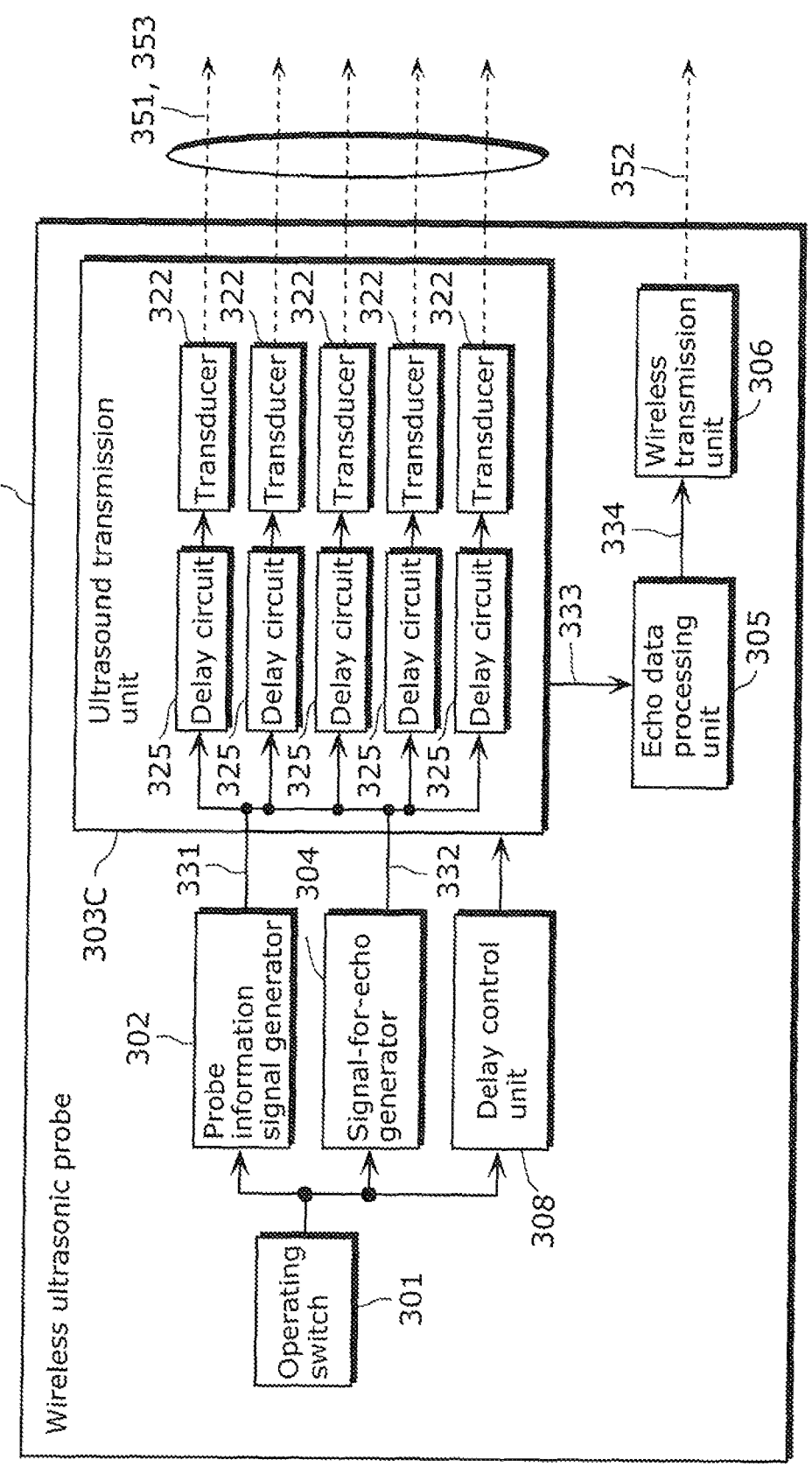
FIG. 14 is a block diagram of a wireless ultrasonic probe according to Embodiment 2 of the present invention.

FIG. 14 is a block diagram showing a structure of a wireless ultrasonic probe 300A according to Embodiment 2 of the present invention. Note that the same elements as those in FIG. 3 are given the same numerical references, and common descriptions are not repeated. Also note that the wireless reception unit 309 is omitted in FIG. 14.

The wireless ultrasonic probe 300A shown in FIG. 14 is different from the wireless ultrasonic probe 300 shown in FIG. 3 in including an ultrasound transmission unit 303C instead of the ultrasound transmission unit 303. In addition, the wireless ultrasonic probe 300A further includes a delay control unit 308.

The ultrasound transmission unit 303C includes a plurality of transducers 322 and a plurality of delay circuits 325 corresponding to the transducers 322 on a one-by-one basis.

The transducers 322 are used for both the transmission of the pairing ultrasound 351 and the transmission and reception of the echo ultrasound 353. The transducers 322 synchronously transmit the pairing ultrasound 351 according to the probe information signal 331. The transducers 322 also synchronously transmit the echo ultrasound 353 according to the signal for echo 332.

The delay circuits 325 delay the probe information signal 331 and the signal for echo 332 that are provided to the transducers 322.

The delay control unit 308 controls the amount of delay caused by the delay circuits 325.

Figure 15:
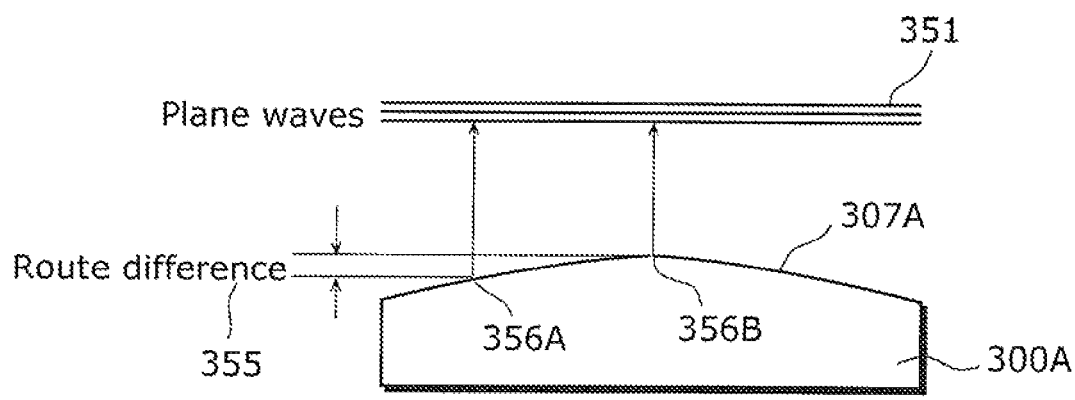
FIG. 15 shows pairing ultrasound according to Embodiment 2 of the present invention.

FIG. 15 shows the pairing ultrasound 351 transmitted by the wireless ultrasonic probe 300A. Here, it is assumed that the wireless ultrasonic probe 300A has a convex shape as shown in FIG. 15.

As shown in FIG. 15, with the wireless ultrasonic probe 300A having an emitting surface 307A that is curved like a convex shape, for example, there is a route difference 355 between the transducers 322. Therefore, when a large number of transducers 322 are simultaneously driven, the route difference 355 causes a delay in the output signals transmitted from the transducers 322, which could lead to a situation where data included in the output signals do not match each other at the reception position of the diagnostic device 400. To prevent such a situation, the delay circuits 325 delay the probe information signal 331 provided to the transducers 322 so that the route difference 355 is corrected.

Furthermore, the delay control unit 308 adjusts the amount of delay caused by the delay circuits 325 so that the pairing ultrasound 351 becomes plane waves as shown in FIG. 15. More specifically, the transducer 322 at a position 356A in FIG. 15 is the first transducer to transmit ultrasound. At a time when the transmitted ultrasound has traveled the distance of the route difference 355, the transducer 322 at a position 356B in FIG. 15 transmits ultrasound. This allows the ultrasound output from the transducers 322 to be transmitted as plane waves. Such a structure increases the signal level of the pairing ultrasound 351 transmitted from the wireless ultrasonic probe 300A, thereby increasing the possibility of successful communication between the wireless ultrasonic probe 300A and the diagnostic device 400 using the pairing ultrasound 351 even when the wireless ultrasonic probe 300A and the diagnostic device 400 are distant from each other.

With the wireless ultrasonic probe 300A according to Embodiment 2 of the present invention, it is acceptable to use, as the delay circuits 325, a delay circuit which is normally included in the ultrasonic diagnostic apparatus for use in the beamforming performed for generating transmission data.

Figure 16:
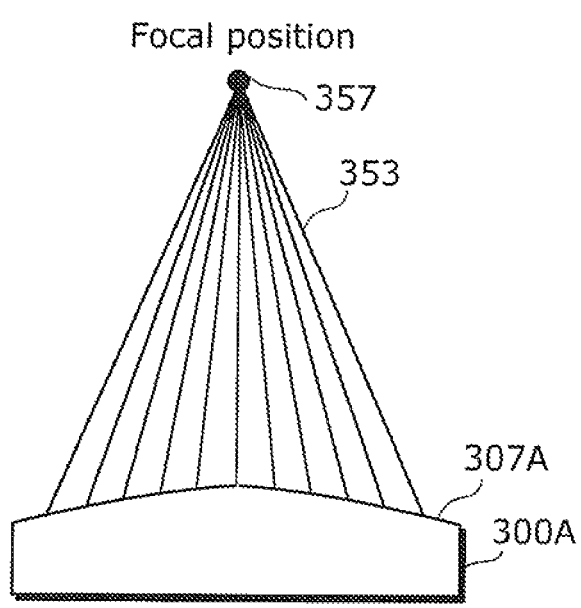
FIG. 16 shows echo ultrasound according to Embodiment 2 of the present invention.

Here, in the process of beamforming, the transducers 322 are driven and the amount of delay is adjusted in such a manner that the signal level of the output signals is maximized at a focal position 357 as shown in FIG. 16. In other words, the delay control unit 308 adjusts the amount of delay caused by the delay circuits 325 so that the focal position 357 of the echo ultrasound 353 matches a predetermined position as shown in FIG. 16.

In such a manner, the wireless ultrasonic diagnostic apparatus 30 according to Embodiment 2 of the present invention uses, for adjusting the delay of the pairing ultrasound 351, the delay circuits normally included in the ultrasonic diagnostic apparatus, thereby increasing the possibility of successful communication between the wireless ultrasonic probe 300A and the diagnostic device 400 using the pairing ultrasound 351 while suppressing an increase in cost.

Figure 17:
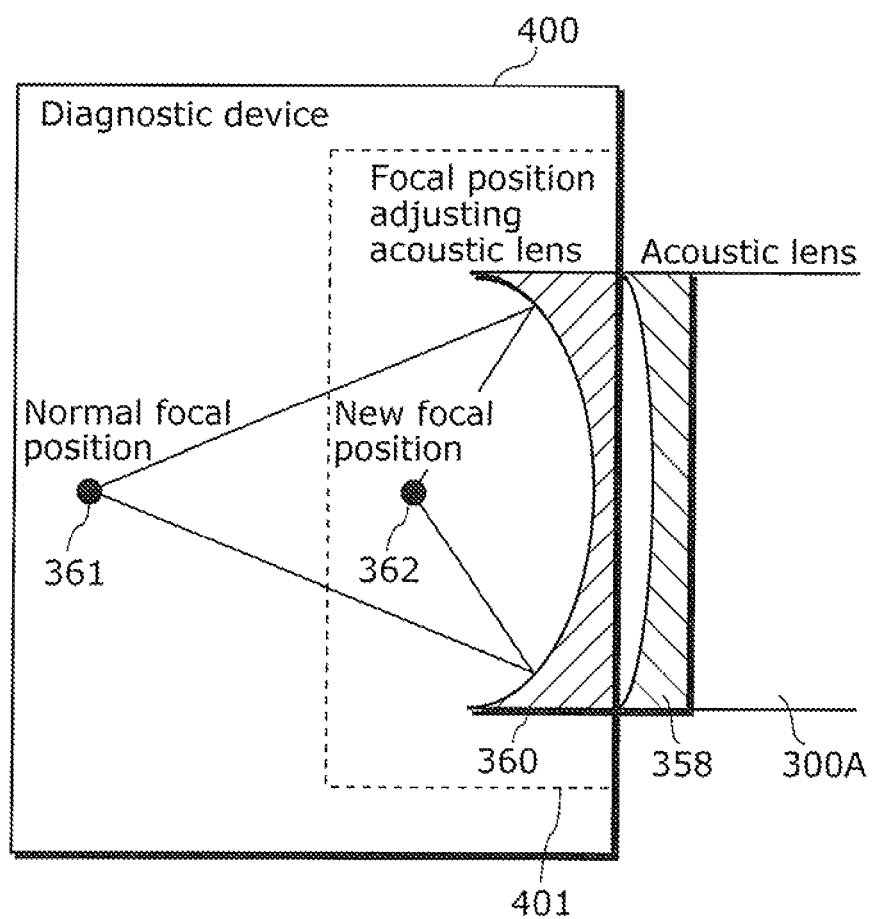
FIG. 17 shows a structure of an ultrasound reception unit according to Embodiment 2 of the present invention.

FIG. 17 shows a structure of the ultrasound reception unit 401 included in the diagnostic device 400 according to Embodiment 2 of the present invention.

Here, the pairing ultrasound 351 preferably comes into a focus in a shorter distance. To bring the focal position closer, the ultrasound reception unit 401 may include a focal position adjusting acoustic lens 360 which adjusts the focal length as shown in FIG. 17.

General wireless ultrasonic probes include an acoustic lens 358 so that the focal position is at several centimeters ahead within the body. Thus, when the ultrasound reception unit 401 does not include the focal position adjusting acoustic lens 360, the focal position of the pairing ultrasound 351 is at a focal position 361 shown in FIG. 17. On the other hand, when the ultrasound reception unit 401 includes the focal position adjusting acoustic lens 360, the focal position of the pairing ultrasound 351 is at a focal position 362 shown in FIG. 17.

By bringing the focal position closer in such a manner, it is possible to reduce attenuation of the pairing ultrasound 351, thereby increasing the possibility of successful communication between the wireless ultrasonic probe 300A and the diagnostic device 400 using the pairing ultrasound 351.

Next, a flow of the operation of the wireless ultrasonic probe 300A is described.

Figure 18:
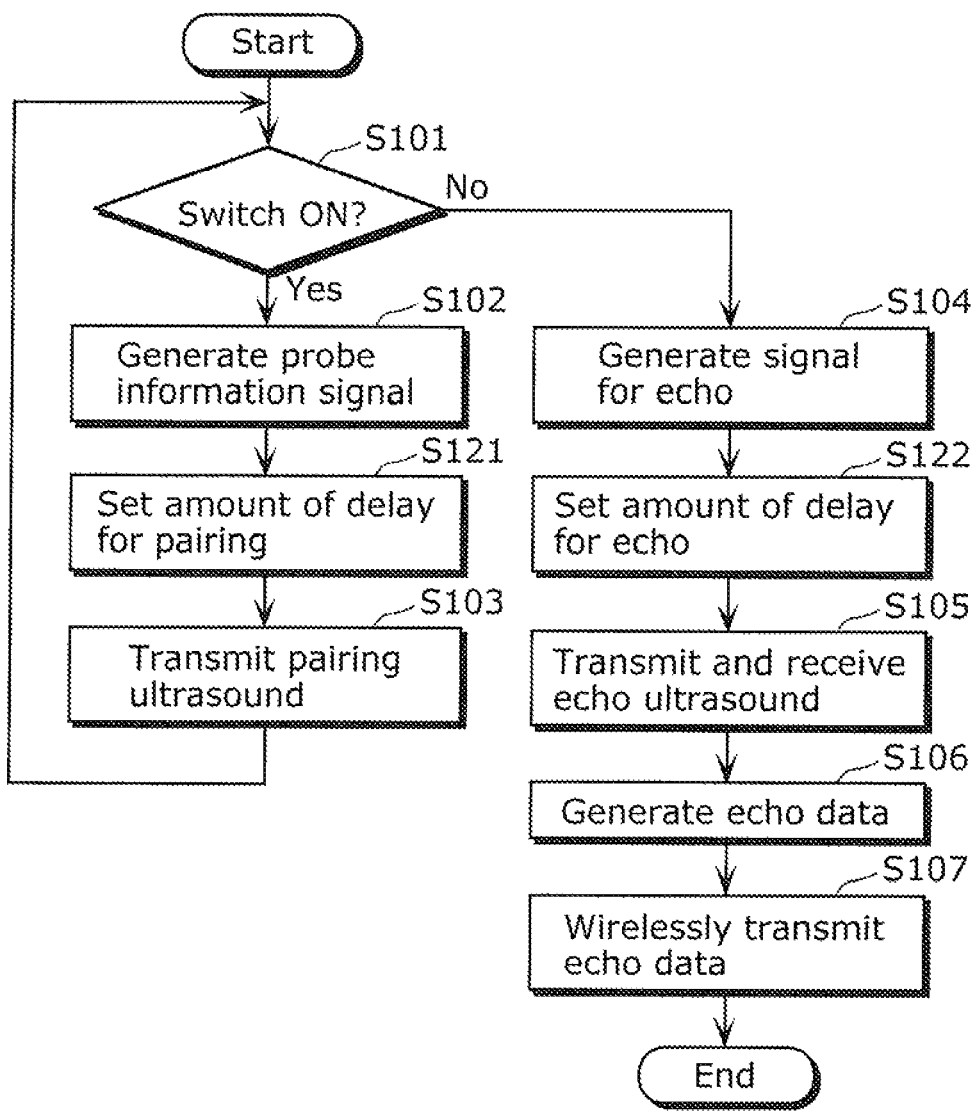
FIG. 18 is a flowchart showing a processing flow of a wireless ultrasonic probe according to Embodiment 2 of the present invention.

FIG. 18 is a flowchart showing the flow of the operation of the wireless ultrasonic probe 300A. Note that the same processing as that in FIG. 10 are given the same numerical references. FIG. 18 shows Steps S121 and S122 in addition to the processing shown in FIG. 10.

As shown in FIG. 18, when the operating switch 301 is on (Yes in S101), the probe information signal generator 302 generates the probe information signal 331 (S102).

Next, the delay control unit 308 sets the amount of delay to be caused by the delay circuits 325 to an amount of delay for pairing so that the pairing ultrasound 351 becomes plane waves (S121).

Next, the ultrasound transmission unit 303 transmits, as the pairing ultrasound 351, the probe information signal 331 delayed by the delay circuits 325 (S103).

On the other hand, when the operating switch 301 is off (No in S101), the signal-for-echo generator 304 generates the signal for echo 332 (S104).

Next, the delay control unit 308 sets the amount of delay to be caused by the delay circuits 325 to an amount of delay for echo so that the focal position of the echo ultrasound 353 matches a predetermined position (S122).

Subsequently, the ultrasound transmission unit 303 transmits, as the echo ultrasound 353, the signal for echo 332 delayed by the delay circuits 325 (S105).

Then, the ultrasound transmission unit 303 receives the reflected waves 354 that are the echo ultrasound 353 reflected from the subject, and outputs the reflected waves 354 as the echo signal 333. Next, the echo data processing unit 305 generates the echo data 334 from the echo signal 333 (S106).

Subsequently, the wireless transmission unit 306 wirelessly transmits the echo data 334 as the echo data 352 (S107).

Although it has been described above that the wireless ultrasonic probe 300A has a convex shape, the wireless ultrasonic probe 300A may have a different shape. In that case, it is sufficient as long as the delay circuits 325 delay, according to the shape of the emitting surface 307A of the wireless ultrasonic probe 300A, the probe information signal 331 provided to the transducers 322 so that the pairing ultrasound 351 synchronously transmitted by the transducers 322 becomes plane waves.

Although it has also been described above that all the transducers 322 included in the ultrasound transmission unit 303C are used for the generation of both the pairing ultrasound 351 and the echo ultrasound 353, the ultrasound transmission unit 303C may include a transducer dedicated for the pairing ultrasound 351 or a transducer dedicated for the echo ultrasound 353.

Embodiment 3

Embodiment 3 of the present invention describes application of the present invention to a mechanical sector-scanning wireless ultrasonic probe.

Figure 19:
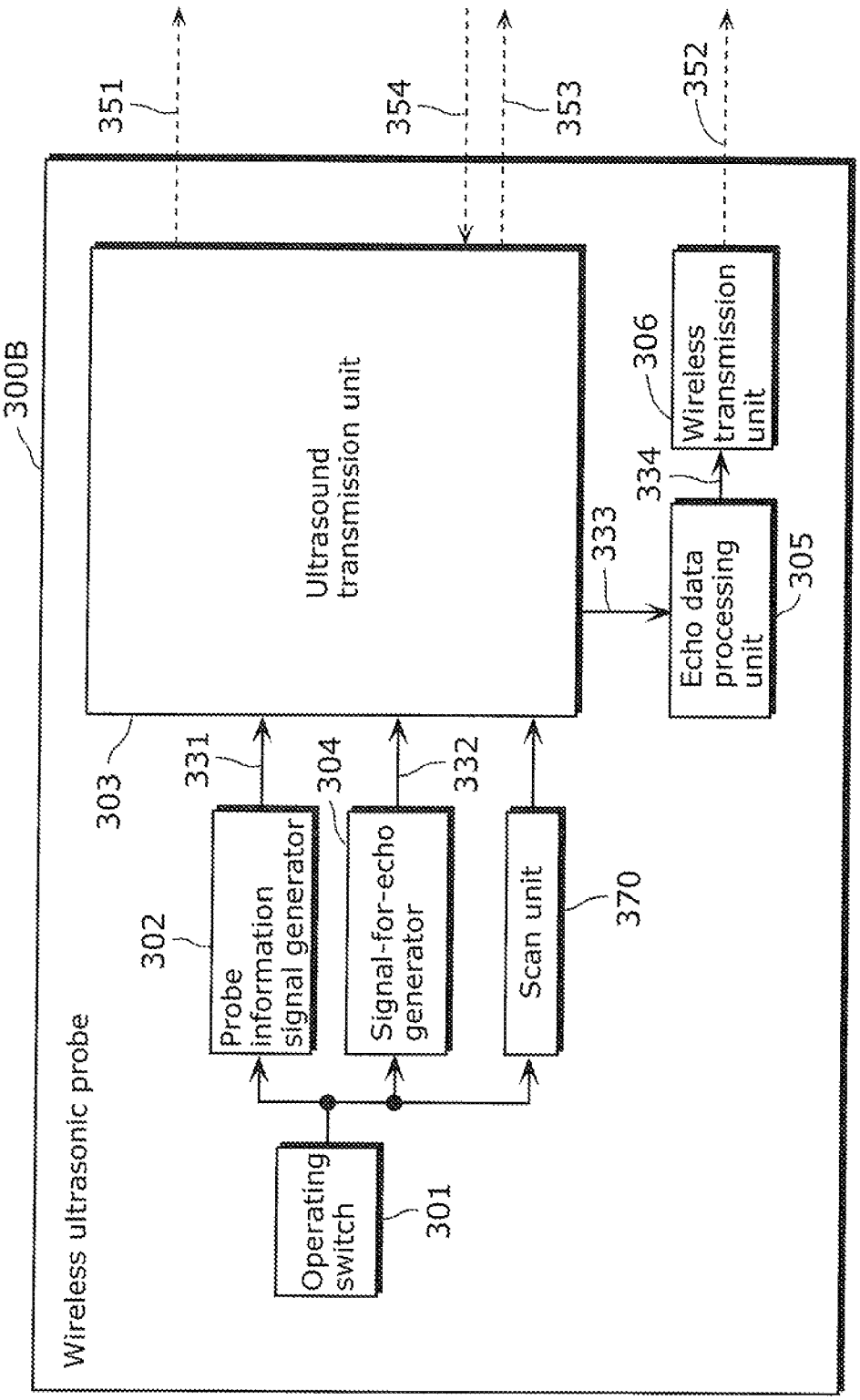
FIG. 19 is a block diagram of a wireless ultrasonic probe according to Embodiment 3 of the present invention.

FIG. 19 is a block diagram showing a structure of a wireless ultrasonic probe 300B according to Embodiment 3 of the present invention. Note that the same elements as those in FIG. 3 are given the same numerical references, and common descriptions are not repeated. Also note that the wireless reception unit 309 is omitted in FIG. 19.

The wireless ultrasonic probe 300B shown in FIG. 19 includes a scan unit 370 in addition to the constituent elements of the wireless ultrasonic probe 300 shown in FIG. 3.

When the ultrasound transmission unit 303 transmits the echo ultrasound 353, the scan unit 370 performs sector scanning in directions in which the echo ultrasound 353 is transmitted. In addition, when the ultrasound transmission unit 303 transmits the pairing ultrasound 351, the scan unit 370 fixes the direction in which the pairing ultrasound 351 is transmitted.

More specifically, when the operating switch 301 is pressed, the scan unit 370 causes the transducer at the tip of the wireless ultrasonic probe 300B to pause at the position directly in front of the diagnostic device 400. This enables the mechanical sector-scanning wireless ultrasonic probe 300B to reliably perform the pairing.

Next, a flow of the operation of the wireless ultrasonic probe 300B is described.

Figure 20:
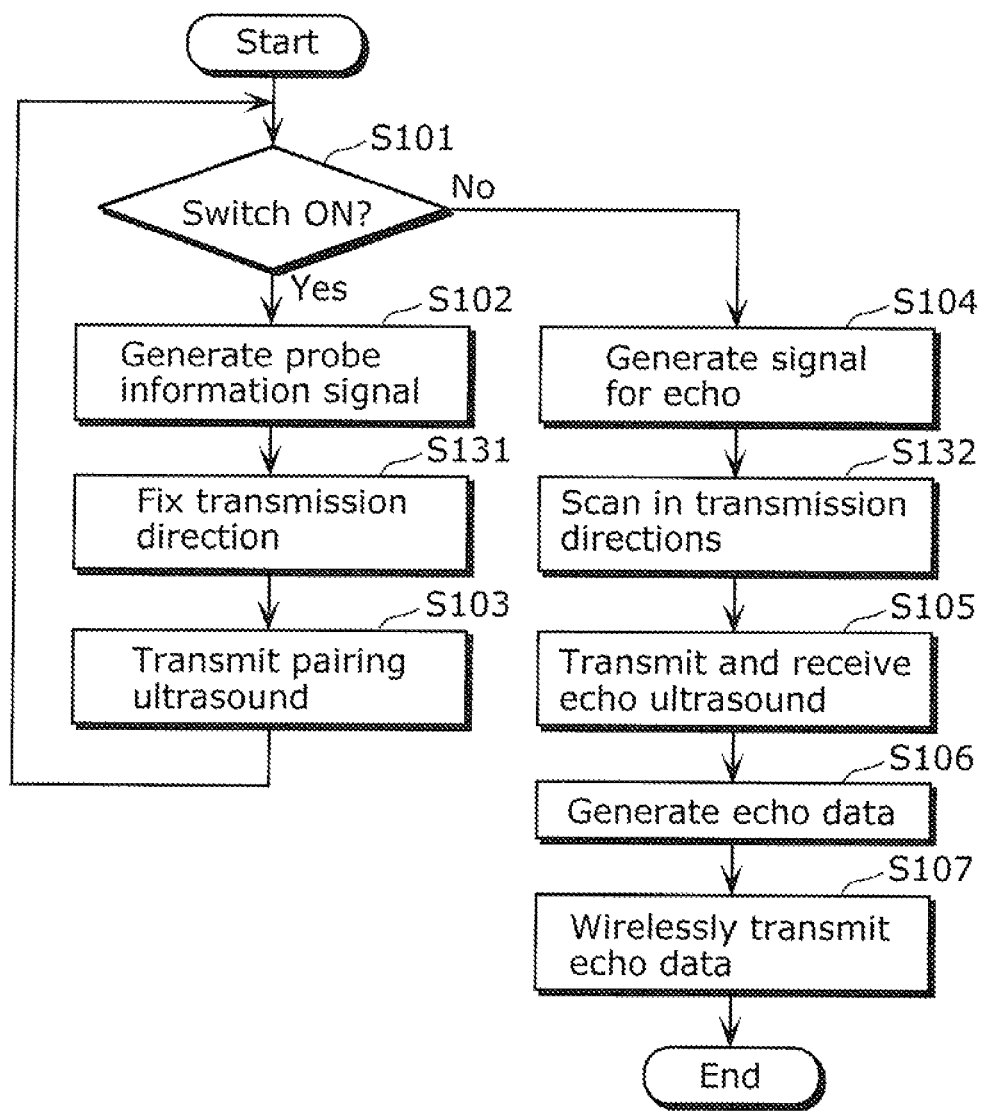
FIG. 20 is a flowchart showing a processing flow of a wireless ultrasonic probe according to Embodiment 3 of the present invention.

FIG. 20 is a flowchart showing the flow of the operation of the wireless ultrasonic probe 300B. Note that the same processing as that in FIG. 10 are given the same numerical references. FIG. 20 shows Steps S131 and S132 in addition to the processing shown in FIG. 10.

As shown in FIG. 20, when the operating switch 301 is on (Yes in S101), the probe information signal generator 302 generates the probe information signal 331 (S102).

Next, the scan unit 370 fixes the direction in which the pairing ultrasound 351 is transmitted (S131).

Then, the ultrasound transmission unit 303 transmits the probe information signal 331 as the pairing ultrasound 351 (S103).

On the other hand, when the operating switch 301 is off (No in S101), the signal-for-echo generator 304 generates the signal for echo 332 (S104).

Next, the scan unit 370 performs scanning in directions in which the echo ultrasound 353 is transmitted (S132).

Subsequently, the ultrasound transmission unit 303 transmits the signal for echo 332 as the echo ultrasound 353 (S105).

Then, the ultrasound transmission unit 303 receives the reflected waves 354 that are the echo ultrasound 353 reflected from the subject, and outputs the reflected waves 354 as the echo signal 333. Next, the echo data processing unit 305 generates the echo data 334 from the echo signal 333 (S106).

Subsequently, the wireless transmission unit 306 wirelessly transmits the echo data 334 as the echo data 352 (S107).

Although the above embodiments describe that the signal-for-echo generator 304 included in the wireless ultrasonic probe generates the signal for echo 332 from which the echo ultrasound 353 is generated, the wireless ultrasonic probe may output, as the signal for echo 332, a transmission signal transmitted from the diagnostic device.

Figure 21:
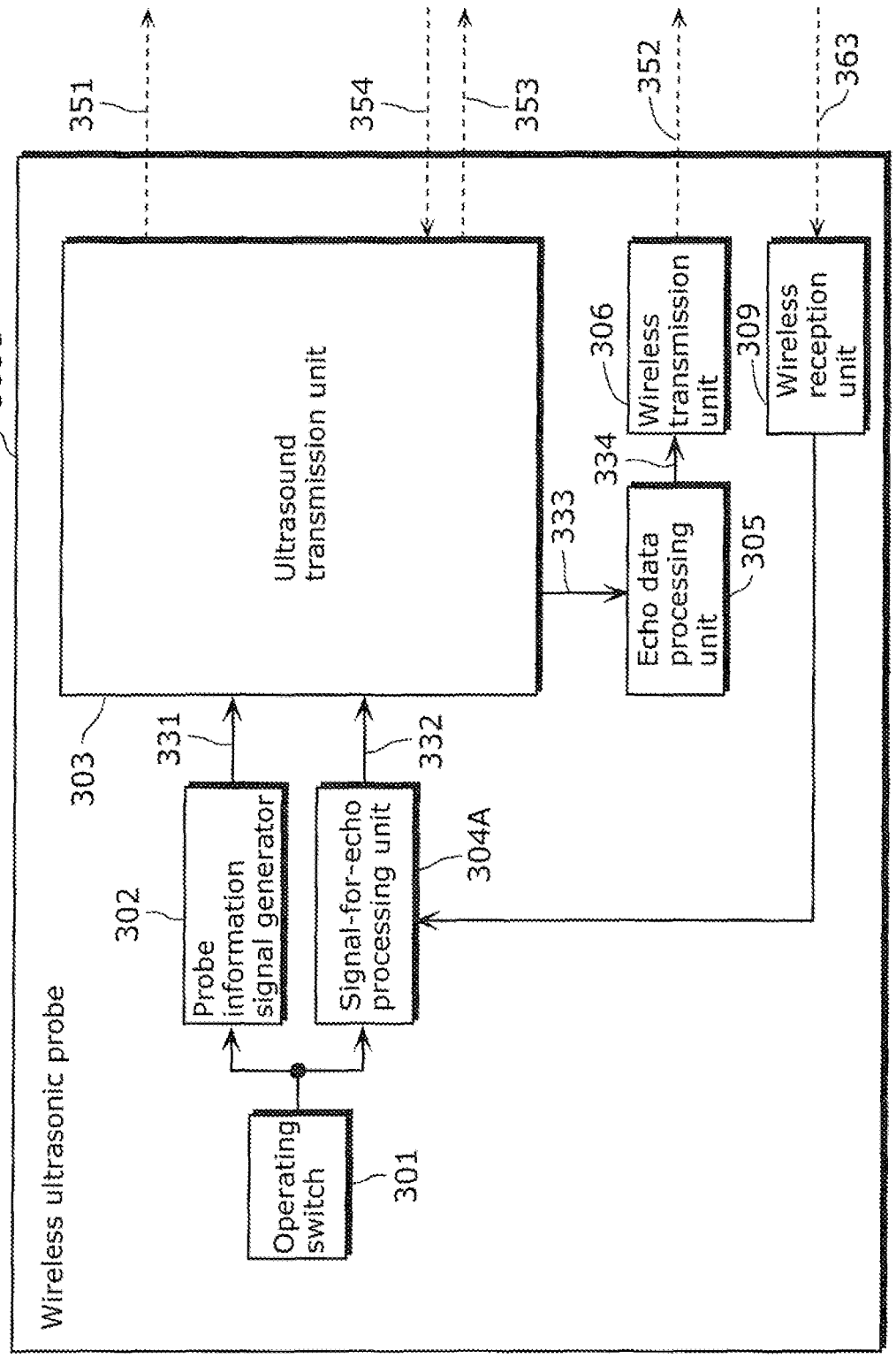
FIG. 21 is a block diagram of a wireless ultrasonic probe according to a variation of the present invention.

FIG. 21 shows a structure of a wireless ultrasonic probe 300C that outputs, as the signal for echo 332, a transmission signal 363 transmitted from the diagnostic device 400.

The wireless ultrasonic probe 300C shown in FIG. 21 is different from the wireless ultrasonic probe 300 shown in FIG. 3 in including a signal-for-echo processing unit 304A instead of the signal-for-echo generator 304. Furthermore, the wireless reception unit 309 receives the transmission signal 363 wirelessly transmitted from the diagnostic device 400.

The signal-for-echo processing unit 304A outputs, as the signal for echo 332, the transmission signal 363 wirelessly transmitted from the diagnostic device 400.

At least some of the processing units included in the wireless ultrasonic diagnostic apparatus 30 according to the above embodiments may be implemented in the form of a Large Scale Integrated (LSI) circuit that is an integrated circuit. These may be implemented in a single chip individually, or in a single chip that includes some or all of them.

Furthermore, the means for circuit integration is not limited to to an LSI, and implementation with a dedicated circuit or a general-purpose processor is also available. It is also acceptable to use a field programmable gate array (FPGA) that is programmable after the LSI has been manufactured, and a reconfigurable processor in which connections and settings of circuit cells within the LSI are reconfigurable.

Some or all of the functions of the wireless ultrasonic diagnostic apparatus 30 according to the embodiments of the present invention may be achieved through execution of a program by a processor such as a CPU.

In addition, the present invention may be realized as the program or a recording medium on which the program is recorded. It is apparent that the program may be distributed via a transmission medium such as the Internet.

Furthermore, it is possible to combine at least some of the functions of the wireless ultrasonic diagnostic apparatus according to Embodiments 1 to 3 and the wireless ultrasonic diagnostic apparatus according to the variation of Embodiments 1 to 3.

The present invention includes various variations achieved through modifications of the embodiments of the present invention that a person skilled in the art could conceive without departing from the scope of the present invention.

INDUSTRIAL APPLICABILITY

The wireless ultrasonic diagnostic apparatus according to the present invention is capable of easily and reliably establishing connection between a wireless ultrasonic probe and a diagnostic device using an ultrasound signal. It is particularly useful as a wireless ultrasonic diagnostic apparatus that uses a plurality of wireless ultrasonic probes.

REFERENCE SIGNS LIST 10, 30 Wireless ultrasonic diagnostic apparatus
100 Ultrasonic probe
110 PS conversion unit
112 Scrambler
114 Code signal generator
116 Modulator
200 Main device
300, 300A, 300B, 300C Wireless ultrasonic probe
301 Operating switch
302 Probe information signal generator
303, 303A, 303B, 303C Ultrasound transmission unit
304 Signal-for-echo generator
304A Signal-for-echo processing unit
305 Echo data processing unit
306 Wireless transmission unit
307, 307A Emitting surface
308 Delay control unit
309 Wireless reception unit
320, 321, 322 Transducer
325 Delay circuit
331, 451 Probe information signal
332 Signal for echo
333 Echo signal
334, 352, 453 Echo data
351 Pairing ultrasound
353 Echo ultrasound
354 Reflected waves
355 Route difference
356A, 356B Position
357, 361, 362 Focal position
358 Acoustic lens
359 Control signal
360 Focal position adjusting acoustic lens
363 Transmission signal
370 Scan unit
400 Diagnostic device
401 Ultrasound reception unit
402 Probe information detection unit
403 Synchronizing signal detection unit
404 Probe information determination unit
405 Probe information setting unit
406 Wireless reception unit
407 Echo data processing unit
408 Display unit
409 Error processing unit
410 Wireless transmission unit
452 Probe information
454 Image data
501 LED
502 Speaker
601 Data signal
602 Header portion
603 Data portion

The invention claimed is:

1. A wireless ultrasonic diagnostic apparatus comprising:
a diagnostic device which comprises a processor or integrated circuit and is configured to receive ultrasound signals and to wirelessly receive data in a frequency band different from ultrasound, under control by the processor or integrated circuit; and
a wireless ultrasonic probe which (i) generates a first signal including probe information for identifying said wireless ultrasonic probe, (ii) transmits the first signal as a pairing ultrasound to said diagnostic device for pairing said wireless ultrasonic probe and said diagnostic device, (iii) transmits an echo ultrasound to a subject, (iv) generates echo data using reflected waves that are the echo ultrasound reflected from the subject, the echo data being generated so as to be associated with the probe information included in the first signal for identifying said wireless ultrasonic probe, and (v) wirelessly transmits, in the frequency band different from ultrasound, the echo data associated with the probe information to said diagnostic device;
wherein said diagnostic device, under control of the processor or integrated circuit, (i) receives the pairing ultrasound transmitted by said wireless ultrasonic probe, detects the probe information from the received pairing ultrasound, and sets the detected probe information, to thereby pair said wireless ultrasonic probe and said diagnostic device, (ii) receives data that is wirelessly transmitted in the frequency band different from ultrasound, (iii) determines whether or not the received data is associated with the set probe information, and determines that the received data is the echo data wirelessly transmitted by said paired wireless ultrasonic probe when it is determined that the received data is associated with the set probe information, and (v) when it is determined that the received data is the echo data wirelessly transmitted by said paired wireless ultrasonic probe, processes the received echo data,
wherein said wireless ultrasonic probe includes a transducer which both (i) transmits the pairing ultrasound according to the first signal and (ii) emits the echo ultrasound,
wherein output of both the pairing ultrasound and the echo ultrasound are controlled in accordance with a single input from an operating switch that is operated by an operator, and
wherein said wireless ultrasonic probe transmits the first signal as the pairing ultrasound to said diagnostic device when the operator provides the operating switch with the single input, in a state in which said wireless ultrasonic probe is in direct physical contact with said diagnostic device, and the pairing ultrasound reaches said diagnostic device only in the state in which said wireless ultrasonic probe is in direct physical contact with said diagnostic device.

2. The wireless ultrasonic diagnostic apparatus according to claim 1, wherein said wireless ultrasonic probe further includes the operating switch, which is operable by the operator, and
wherein when said operating switch is pressed, said wireless ultrasonic probe generates the first signal, and transmits the first signal as the pairing ultrasound.

3. The wireless ultrasonic diagnostic apparatus according to claim 1,
wherein the first signal generated by said wireless ultrasonic probe includes a synchronizing signal, and
wherein said diagnostic device is configured to detect the probe information from the pairing ultrasound by detecting the synchronizing signal included in the received pairing ultrasound.

4. The wireless ultrasonic diagnostic apparatus according to claim 1, wherein said transducer comprises a plurality of transducers which synchronously transmit the pairing ultrasound according to the first signal.

5. The wireless ultrasonic diagnostic apparatus according to claim 4, wherein said wireless ultrasonic probe delays, according to a shape of a surface of said wireless ultrasonic probe from which the pairing ultrasound is emitted, the first signal so that the pairing ultrasound being synchronously transmitted becomes plane waves.

6. The wireless ultrasonic diagnostic apparatus according to claim 5, wherein said wireless ultrasonic probe (i) generates a second signal, (ii) delays the second signal to adjust a focal position of the echo ultrasound, and (iii) generates the echo ultrasound according to the delayed second signal.

7. The wireless ultrasonic diagnostic apparatus according to claim 1, wherein said wireless ultrasonic probe (i) scans, when the echo ultrasound is emitted, in directions in which the echo ultrasound is emitted using a sector scanning method, and (ii) emits the pairing ultrasound in a fixed direction.

8. The wireless ultrasonic diagnostic apparatus according to claim 1, wherein said diagnostic device has an acoustic impedance in a range of 1.5 to $2.0 \times 10^6$ kg/m$^2$s inclusive.

9. The wireless ultrasonic diagnostic apparatus according to claim 1, wherein said diagnostic device includes an acoustic lens which adjusts a focal position of the pairing ultrasound.

10. The wireless ultrasonic diagnostic apparatus according to claim 1, wherein said diagnostic device notifies an operator of error occurrence when an error occurs with the probe information transmitted by said wireless ultrasonic probe.

11. The wireless ultrasonic diagnostic apparatus according to claim 10, wherein said diagnostic device notifies the operator of the error occurrence by causing an LED to flash or by changing a color of the LED.

12. The wireless ultrasonic diagnostic apparatus according to claim 10, wherein said diagnostic device notifies the operator of the error occurrence by beeping.

13. The wireless ultrasonic diagnostic apparatus according to claim 1, wherein said wireless ultrasonic probe transmits the echo ultrasound to the subject and receives the reflected waves, in a state in which the wireless ultrasonic probe is pressed against a body surface of the subject.

14. The wireless ultrasound diagnostic apparatus according to claim 1, wherein said wireless ultrasonic probe comprises a processor or integrated circuit which is configured to receive the input from the operating switch and control the output of the pairing ultrasound and the output of the echo ultrasound according to the input.

15. The wireless ultrasound diagnostic apparatus according to claim 1, wherein the transducer continues to output the pairing ultrasound when instructed by the operating switch to output the pairing ultrasound, and outputs the echo ultrasound without outputting the pairing ultrasound when instructed by the operating switch not to output the pairing ultrasound.

16. The wireless ultrasound diagnostic apparatus according to claim 1, wherein the transducer outputs the pairing ultrasound when the operating switch is pressed, and stops outputting the pairing ultrasound and outputs the echo ultrasound when the operating switch is released.

17. The wireless ultrasound diagnostic apparatus according to claim 1, wherein the transducer outputs the pairing ultrasound when the operating switch is pressed once, and stops outputting the pairing ultrasound and outputs the echo ultrasound when the operating switch is pressed once more.

18. A wireless ultrasonic probe which is capable of wirelessly communicating with a diagnostic device that comprises a processor or integrated circuit and that is configured to receive ultrasound signals and to wirelessly receive data in a frequency band different from ultrasound under control by the processor or integrated circuit, wherein said wireless ultrasonic probe transmits an echo ultrasound to a subject and receives reflected waves that are the echo ultrasound reflected from the subject, said wireless ultrasonic probe comprising:
    a transducer which both (i) transmits the pairing ultrasound according to the first signal and (ii) emits the echo ultrasound;
    a processor or integrated circuit; and
    a non-transitory memory having stored thereon executable instructions, which when executed by the processor or integrated circuit, cause said wireless ultrasonic probe to:
    (i) generate a first signal including probe information for identifying said wireless ultrasonic probe;
    (ii) transmit the first signal as a pairing ultrasound to the diagnostic device for pairing said wireless ultrasonic probe and said diagnostic device;
    (iii) generate echo data using the reflected waves that are the echo ultrasound reflected from the subject, the echo data being generated so as to be associated with the probe information included in the first signal for identifying said wireless ultrasonic probe; and
    (iv) wirelessly transmit, in the frequency band different from ultrasound, the echo data associated with the probe information to the diagnostic device, and wherein output of both the pairing ultrasound and the echo ultrasound are controlled in accordance with a single input from an operating switch that is operated by an operator, and
wherein said wireless ultrasonic probe transmits the first signal as the pairing ultrasound to said diagnostic device when the operator provides the operating switch with the single input, in a state in which said wireless ultrasonic probe is in direct physical contact with said diagnostic device, and the pairing ultrasound reaches said diagnostic device only in the state in which said wireless ultrasonic probe is in direct physical contact with said diagnostic device.

19. A probe pairing and authentication method performed by a wireless ultrasonic diagnostic apparatus, the wireless ultrasonic diagnostic apparatus including: (i) a diagnostic device which comprises a processor or integrated circuit and is configured to receive ultrasound signals and to wirelessly receive data in a frequency band different from ultrasound, under control by the processor or integrated circuit, and (ii) a wireless ultrasonic probe which is configured to transmit ultrasound and to wirelessly transmit data in the frequency band different from ultrasound, wherein the wireless ultrasonic probe transmits an echo ultrasound to a subject and receives reflected waves that are the echo ultrasound reflected from the subject, and wherein the wireless ultrasonic probe comprises a transducer which both (i) transmits the pairing ultrasound according to the first signal and (ii) emits the echo ultrasound, said probe pairing and authentication method comprising:
    generating, by the wireless ultrasonic probe, a first signal including probe information for identifying the wireless ultrasonic probe;
    transmitting, by the wireless ultrasonic probe, the first signal as a pairing ultrasound to the diagnostic device for pairing the wireless ultrasonic probe and the diagnostic device;
    receiving, by the diagnostic device, the pairing ultrasound transmitted by the wireless ultrasonic probe, detecting, by the diagnostic device, the probe information from the received pairing ultrasound, and setting the detected probe information, to thereby pair the wireless ultrasonic probe and the diagnostic device;

generating, by the wireless ultrasonic probe, echo data using the reflected waves that are the echo ultrasound reflected from the subject, the echo data being generated so as to be associated with the probe information included in the first signal for identifying the wireless ultrasonic probe;

wirelessly transmitting, by the wireless ultrasonic probe, the echo data associated with the probe information, to the diagnostic device, in the frequency band different from ultrasound;

receiving, by the diagnostic device, data that is wirelessly transmitted;

determining, by the diagnostic device, whether or not the received data is associated with the set probe information, and determining that the received data is the echo data wirelessly transmitted by the paired wireless ultrasonic probe when it is determined that the received data is associated with the set probe information; and when it is determined that the received data is the echo data wirelessly transmitted by said paired wireless ultrasonic probe, processing the received echo data, wherein output of both the pairing ultrasound and the echo ultrasound are controlled in accordance with a single input from an operating switch that is operated by an operator, and wherein said wireless ultrasonic probe transmits the first signal as the pairing ultrasound to said diagnostic device when the operator provides the operating switch with the single input, in a state in which said wireless ultrasonic probe is in direct physical contact with said diagnostic device, and the pairing ultrasound reaches said diagnostic device only in the state in which said wireless ultrasonic probe is in direct physical contact with said diagnostic device.

20. The wireless diagnostic apparatus according to claim 1, wherein the pairing ultrasound is transmitted in a first frequency band, and the echo ultrasound is transmitted in a second frequency band different from the first frequency band.

21. The wireless ultrasonic diagnostic apparatus according to claim 20, wherein the second frequency band is higher than the first frequency band.

22. The wireless ultrasonic diagnostic apparatus according to claim 20,
wherein the first frequency band and the second frequency band are between 1 MHz and 20 MHz inclusive.

23. The wireless ultrasonic diagnostic apparatus according to claim 22, wherein the frequency band used for wireless transmission and reception of the echo data is on the order of GHz.

24. A wireless ultrasonic diagnostic apparatus comprising:
a diagnostic device which comprises a processor or integrated circuit and is configured to receive ultrasound signals and to wirelessly receive data in a frequency band different from ultrasound, under control by the processor or integrated circuit; and a wireless ultrasonic probe which (i) generates a first signal including probe information for identifying said wireless ultrasonic probe, (ii) transmits the first signal as a pairing ultrasound to said diagnostic device for pairing said wireless ultrasonic probe and said diagnostic device, (iii) transmits an echo ultrasound to a subject, (iv) generates echo data using reflected waves that are the echo ultrasound reflected from the subject, the echo data being generated so as to be associated with the probe information included in the first signal for identifying said wireless ultrasonic probe, and (v) wirelessly transmits, in the frequency band different from ultrasound, the echo data associated with the probe information to said diagnostic device;

wherein said diagnostic device, under control of the processor or integrated circuit, (i) receives the pairing ultrasound transmitted by said wireless ultrasonic probe, detects the probe information from the received pairing ultrasound, and sets the detected probe information, to thereby pair said wireless ultrasonic probe and said diagnostic device, (ii) receives data that is wirelessly transmitted in the frequency band different from ultrasound, (iii) determines whether or not the received data is associated with the set probe information, and determines that the received data is the echo data wirelessly transmitted by said paired wireless ultrasonic probe when it is determined that the received data is associated with the set probe information, and (v) when it is determined that the received data is the echo data wirelessly transmitted by said paired wireless ultrasonic probe, processes the received echo data, wherein output of the pairing ultrasound is controlled in accordance with a single input from an operating switch that is operated by an operator, and wherein said wireless ultrasonic probe transmits the first signal as the pairing ultrasound to said diagnostic device when the operator provides the operating switch with the single input, in a state in which said wireless ultrasonic probe is in direct physical contact with said diagnostic device, and the pairing ultrasound reaches said diagnostic device only in the state in which said wireless ultrasonic probe is in physical contact with said diagnostic device.

* * * * *